(12) United States Patent
Goff et al.

(10) Patent No.: US 7,886,661 B1
(45) Date of Patent: Feb. 15, 2011

(54) RADIAL COMPRESSION MECHANISM

(76) Inventors: Ed Goff, 4718 N. 33rd St., Phoenix, AZ (US) 85018; Jeremiah J. Warriner, 6220 S. 44th Dr., Laveen, AZ (US) 85339; Justin Knight, 1222 W. 14th St., Tempe, AZ (US) 85281

( * ) Notice: Subject to any disclaimer, the term of this patent is extended or adjusted under 35 U.S.C. 154(b) by 342 days.

(21) Appl. No.: 12/027,059

(22) Filed: Feb. 6, 2008

Related U.S. Application Data

(60) Provisional application No. 60/888,662, filed on Feb. 7, 2007.

(51) Int. Cl.
*B30B 7/04* (2006.01)
*B21J 7/16* (2006.01)
*B21D 41/04* (2006.01)

(52) U.S. Cl. .................. 100/232; 100/291; 100/292; 72/402; 29/508; 29/516; 29/237; 29/283.5

(58) Field of Classification Search ................ 100/232, 100/237, 291, 292; 72/354.2, 402, 409.09, 72/409.1; 29/237, 282, 283.5, 508, 516; 81/313; 425/392, 397, 402
See application file for complete search history.

(56) References Cited

U.S. PATENT DOCUMENTS

| | | | | |
|---|---|---|---|---|
| 5,715,723 | A * | 2/1998 | Owens | 72/402 |
| 6,360,577 | B2 * | 3/2002 | Austin | 72/402 |
| 6,629,350 | B2 * | 10/2003 | Motsenbocker | 29/283.5 |

\* cited by examiner

*Primary Examiner*—Jimmy T Nguyen
(74) *Attorney, Agent, or Firm*—Parsons & Goltry; Robert A. Parsons; Michael W. Goltry

(57) ABSTRACT

Radial compression mechanism includes a base member and a plurality of elongated compression dies. The dies are arranged in a generally circular orientation on the base member with a contact surface of each die in sliding contact with a base surface of an adjacent die. A portion of each base surface of each die cooperates with portions of base surfaces of adjacent dies to define a generally cylindrical central cavity moved between open and closed positions by a driving mechanism. The dies are cammingly coupled to the base member and to the driving mechanism so that rotation of the driving mechanism about the central axis causes each die to move generally arcuately about a point of camming engagement with the base member.

17 Claims, 23 Drawing Sheets

Present Invention with Dies Connected via a Link to Common Base Member

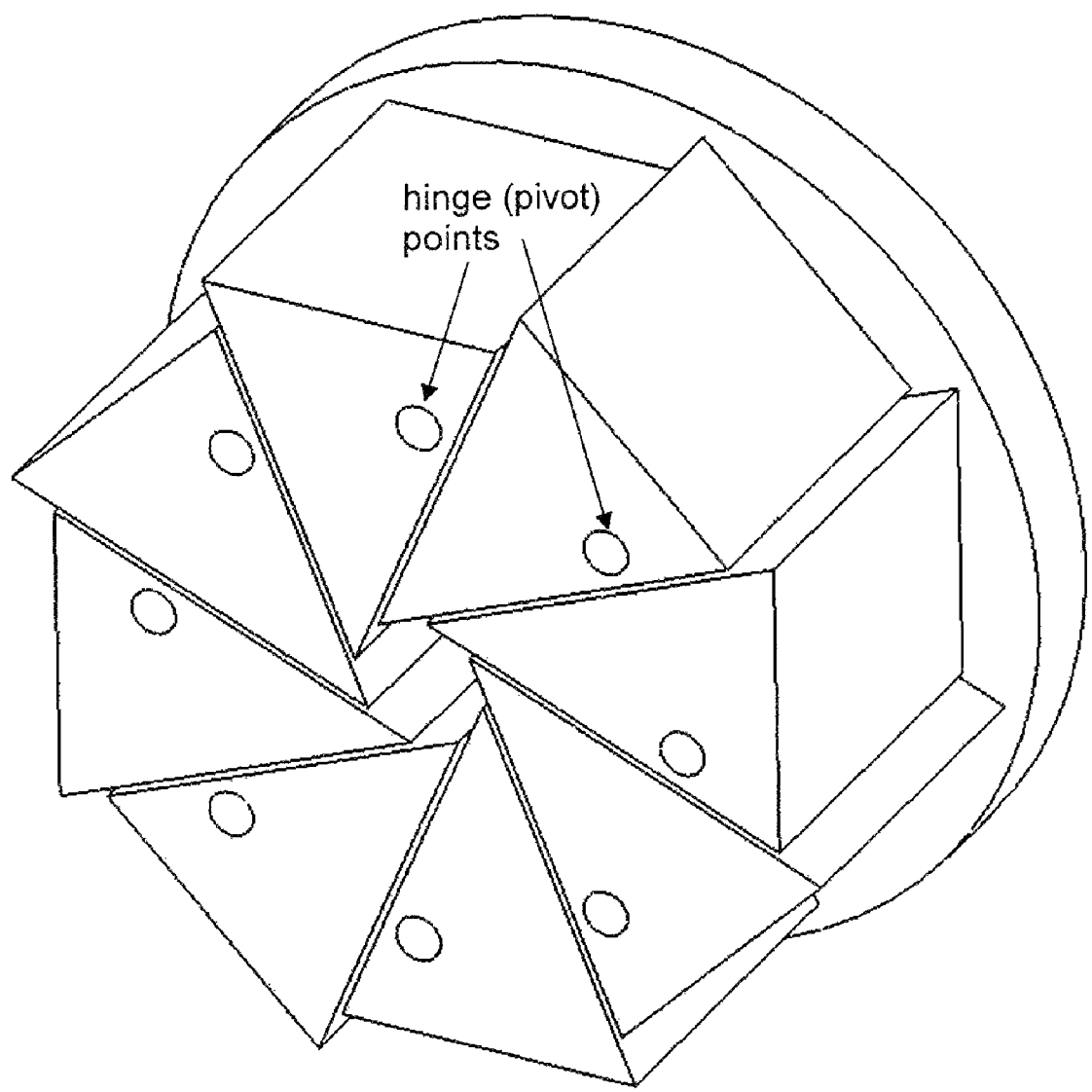
Figure 1 Prior Art Type A – Hinged Dies With Planar Wedge-Shaped Working Surfaces

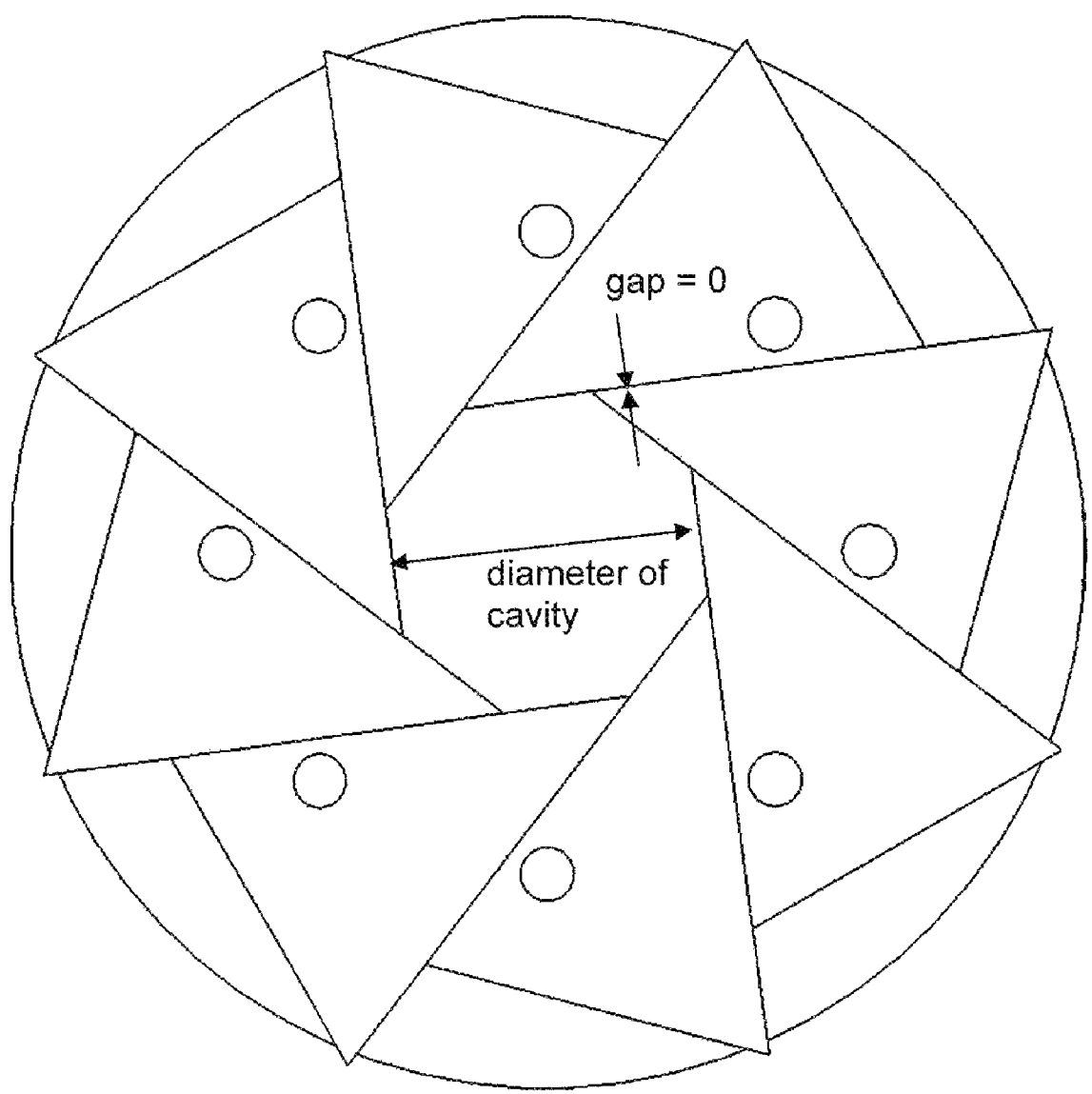
Figure 2 - Prior Art Type A in Fully-Open Position

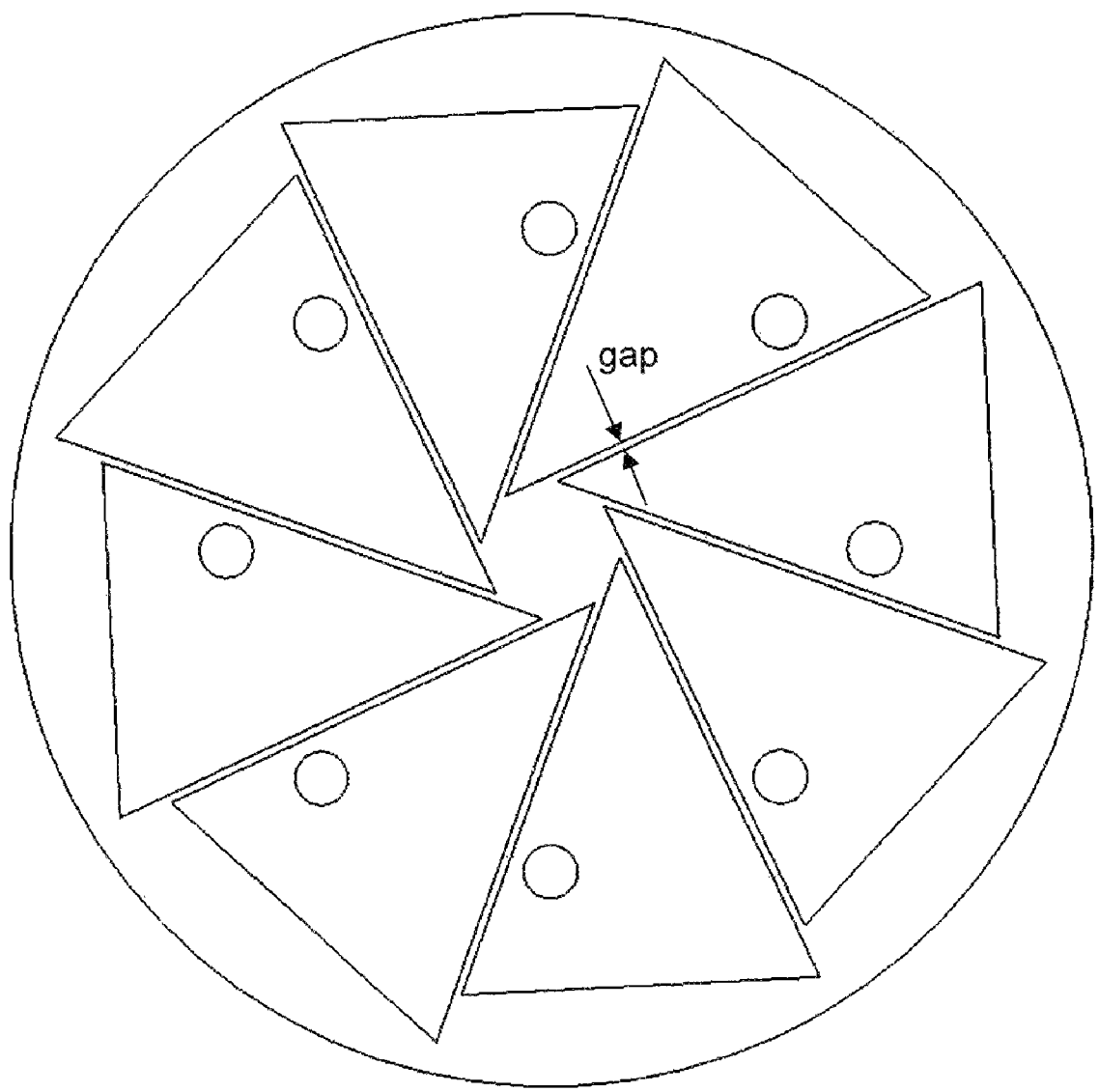
Figure 3 - Prior Art Type A in Partly-Open Position

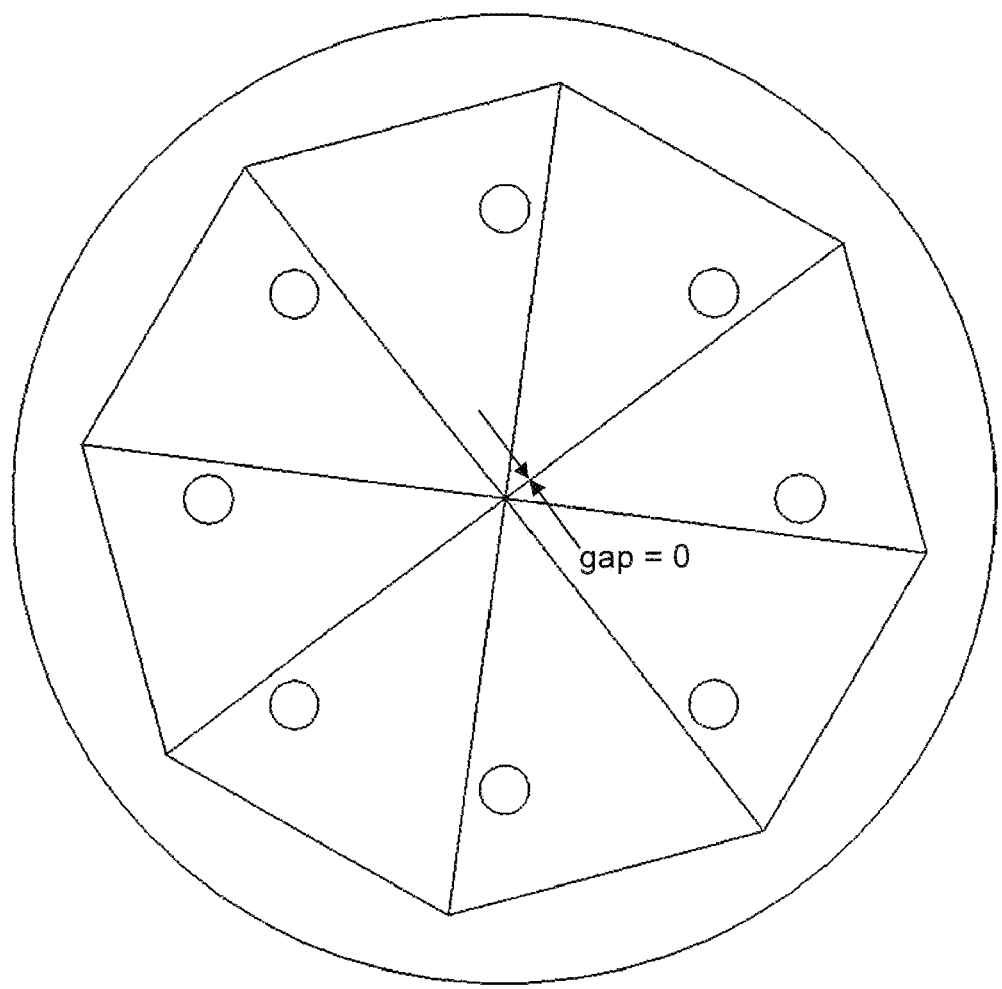
Figure 4 - Prior Art Type A in Fully-Closed Position
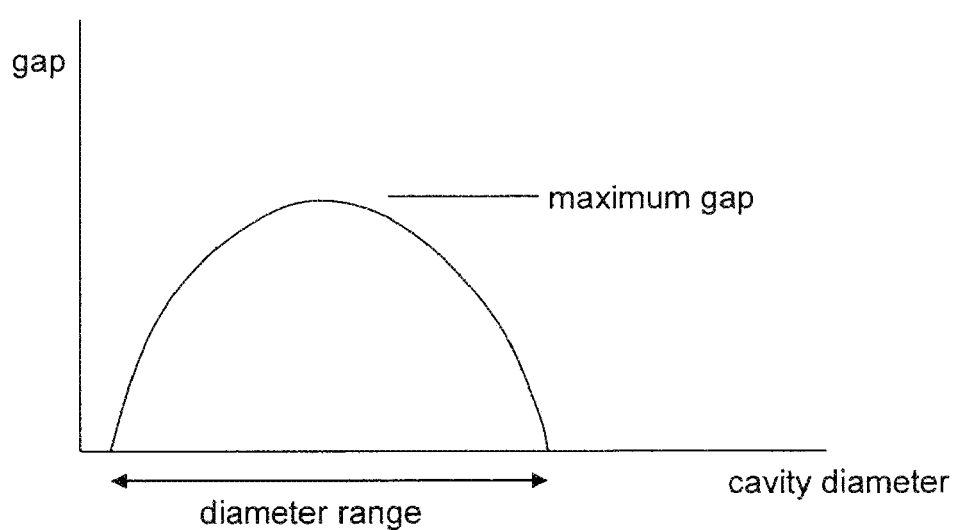
Figure 5 - Prior Art Type A - Relationship Between Diameter and Gap

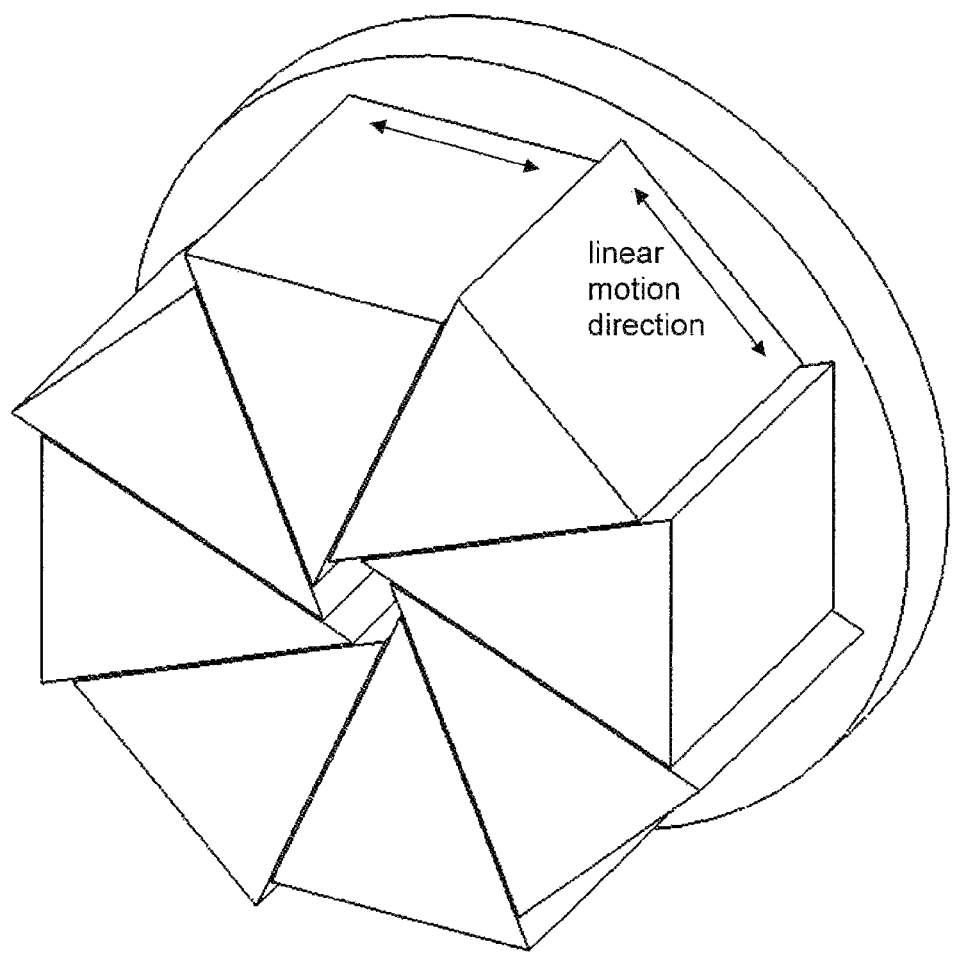
Figure 6 - Prior Art Type B – Linearly-Moving Dies With Planar Wedge-Shaped Working Surfaces

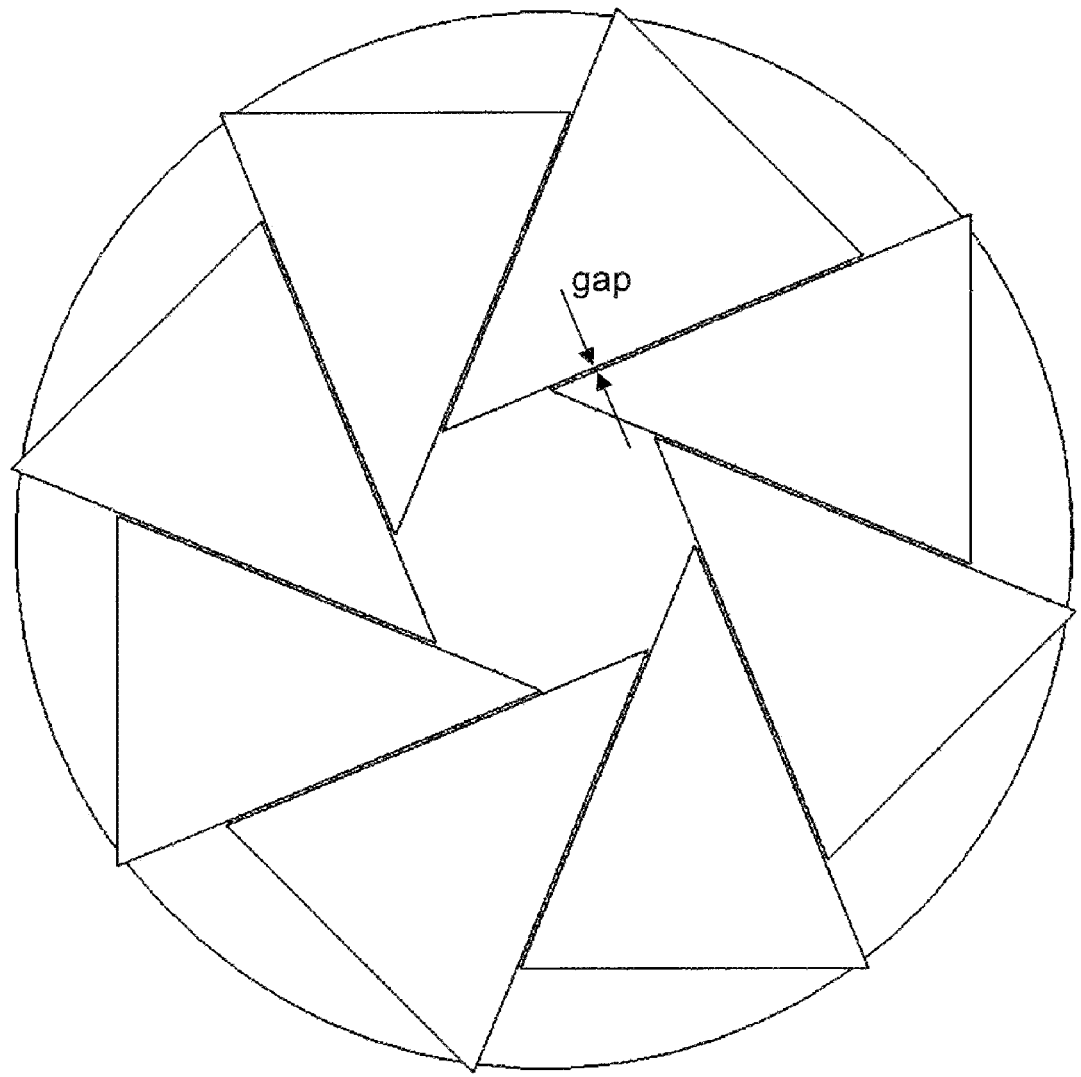
Figure 7 – Prior Art Type B in Fully-Open Position

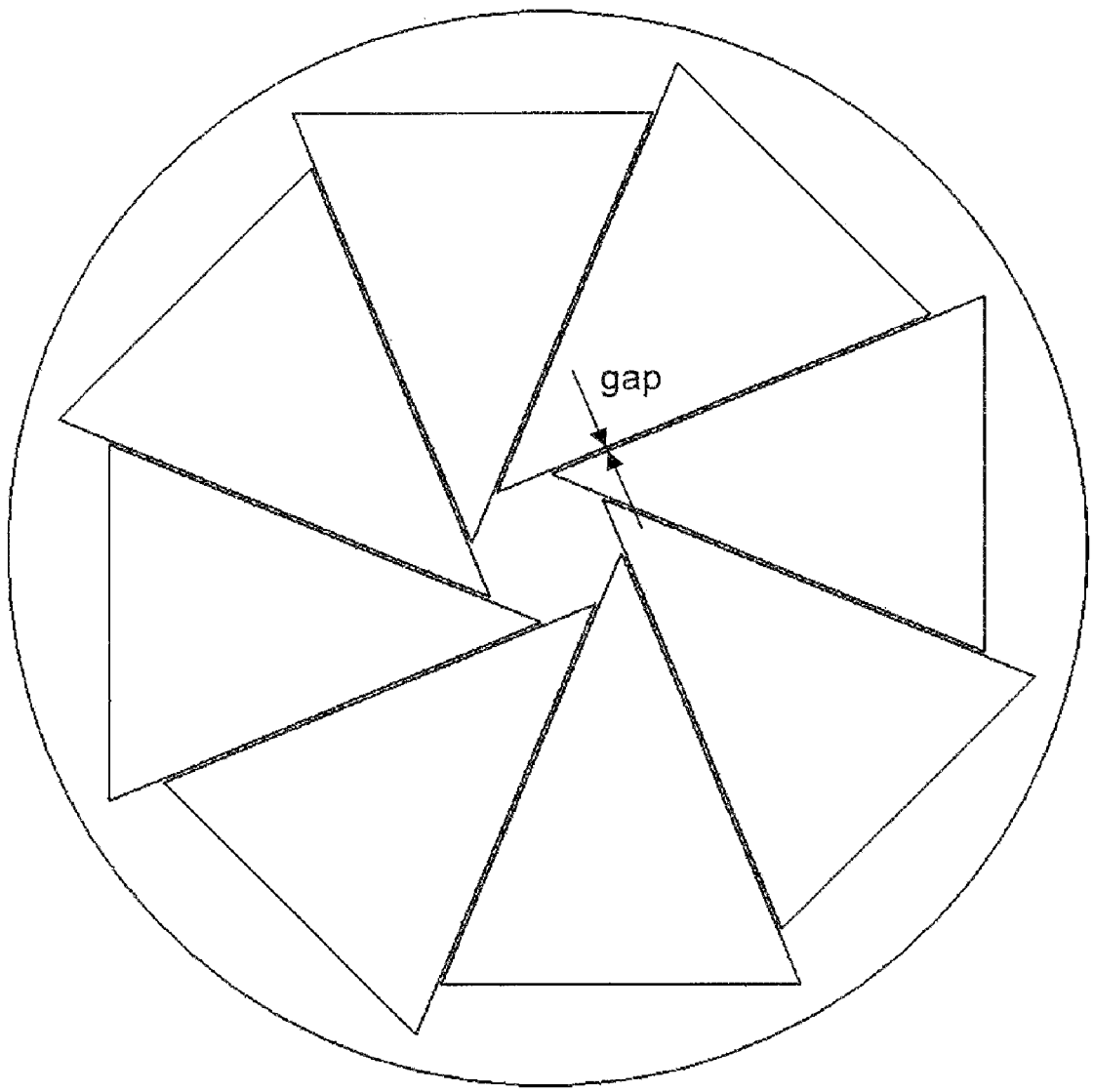
Figure 8 - Prior Art Type B in Partly-Open Position

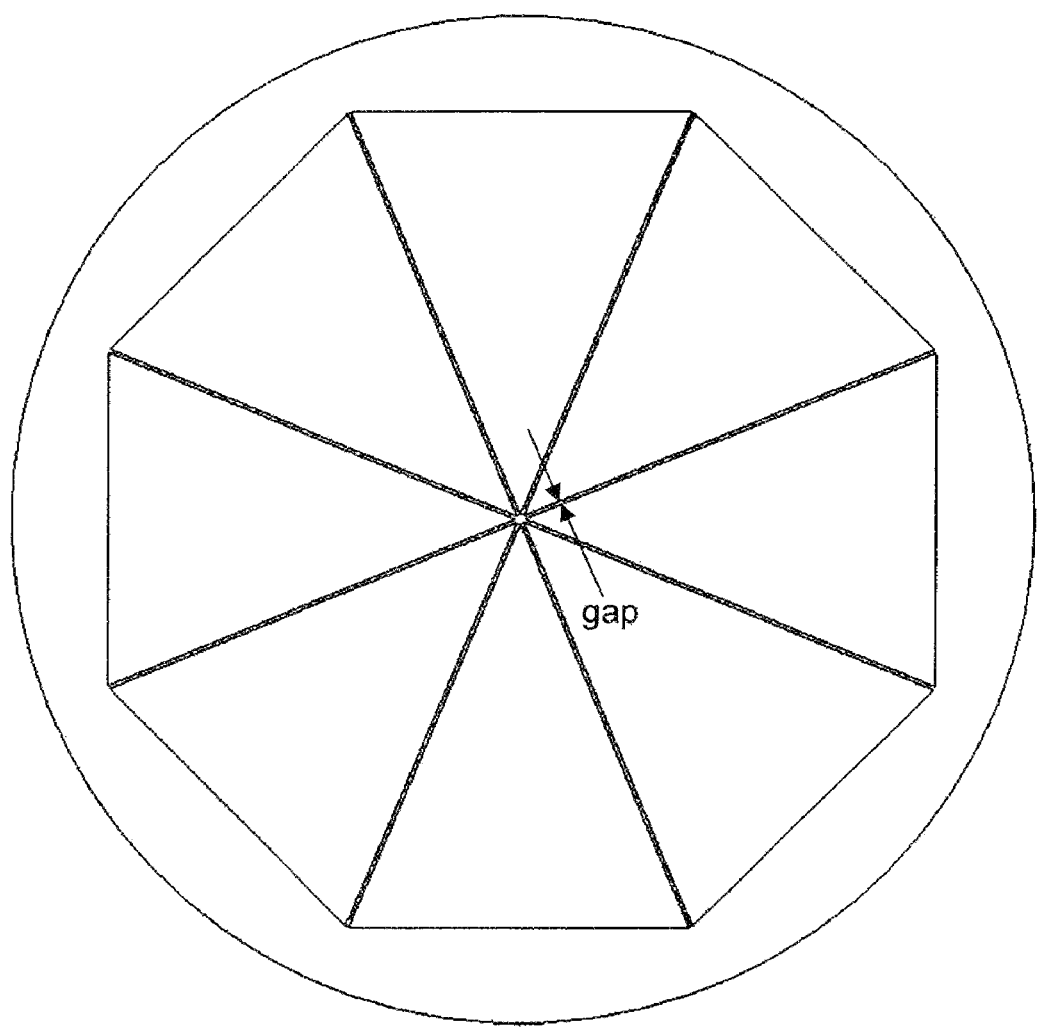
Figure 9 - Prior Art Type B in Fully-Closed Position
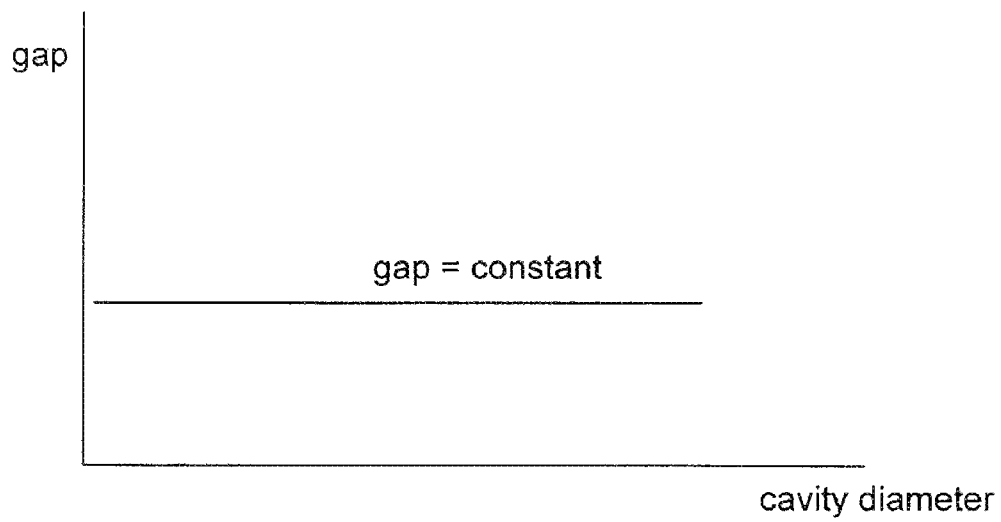
Figure 10 - Prior Art Type B - Relationship Between Diameter and Gap

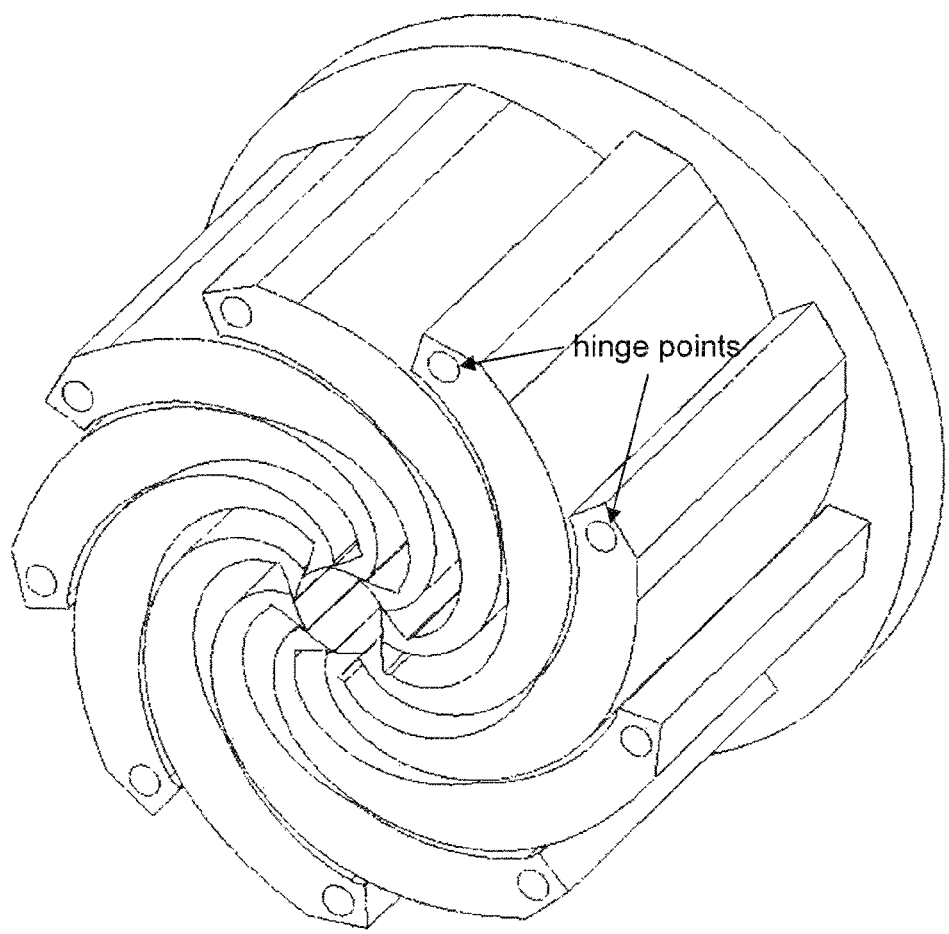
Figure 11 - Prior Art Type C – Hinged Dies with non-planar surfaces designed to have constant gap

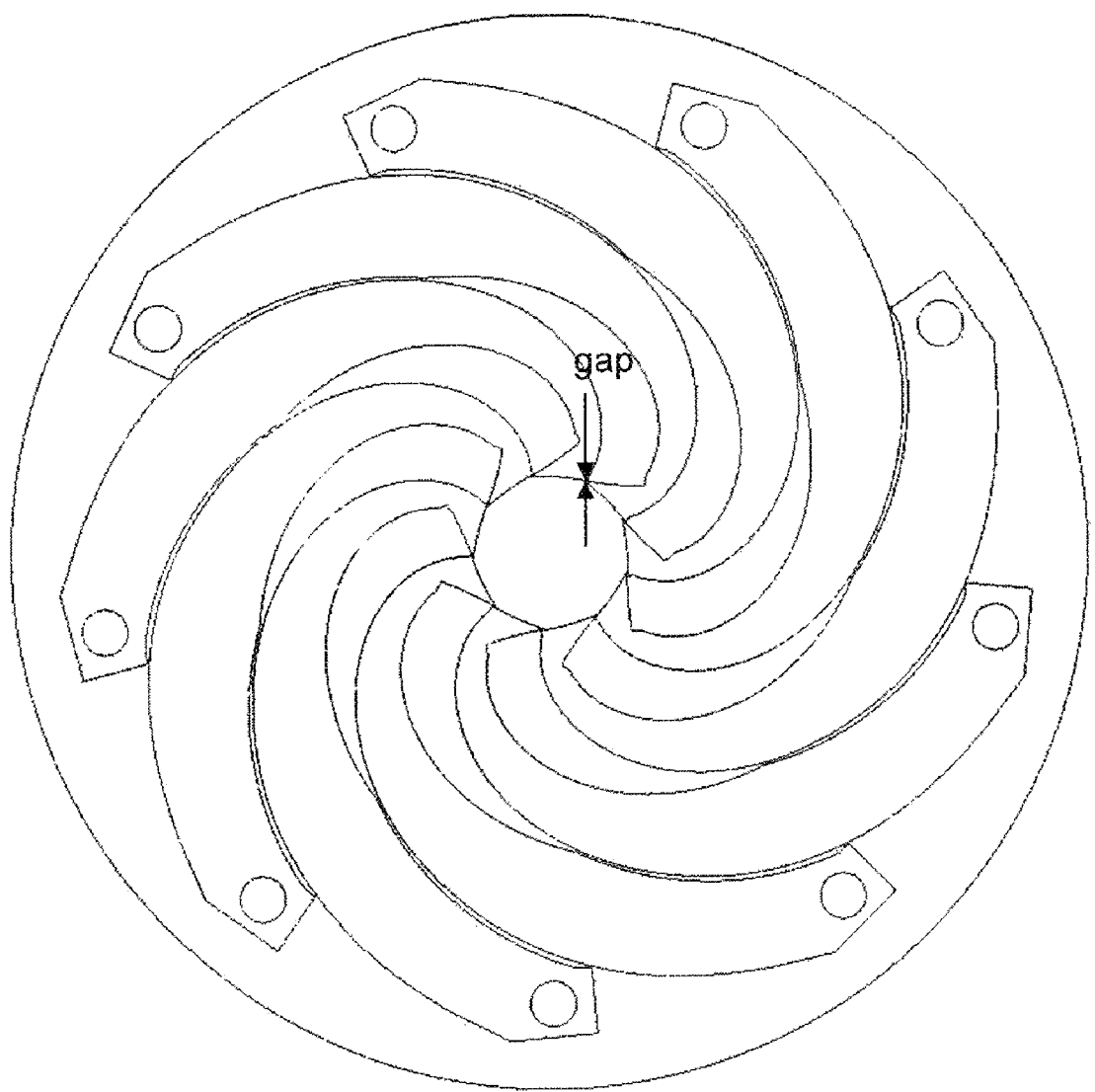
Figure 12 - Prior Art Type C in Fully-Open Position

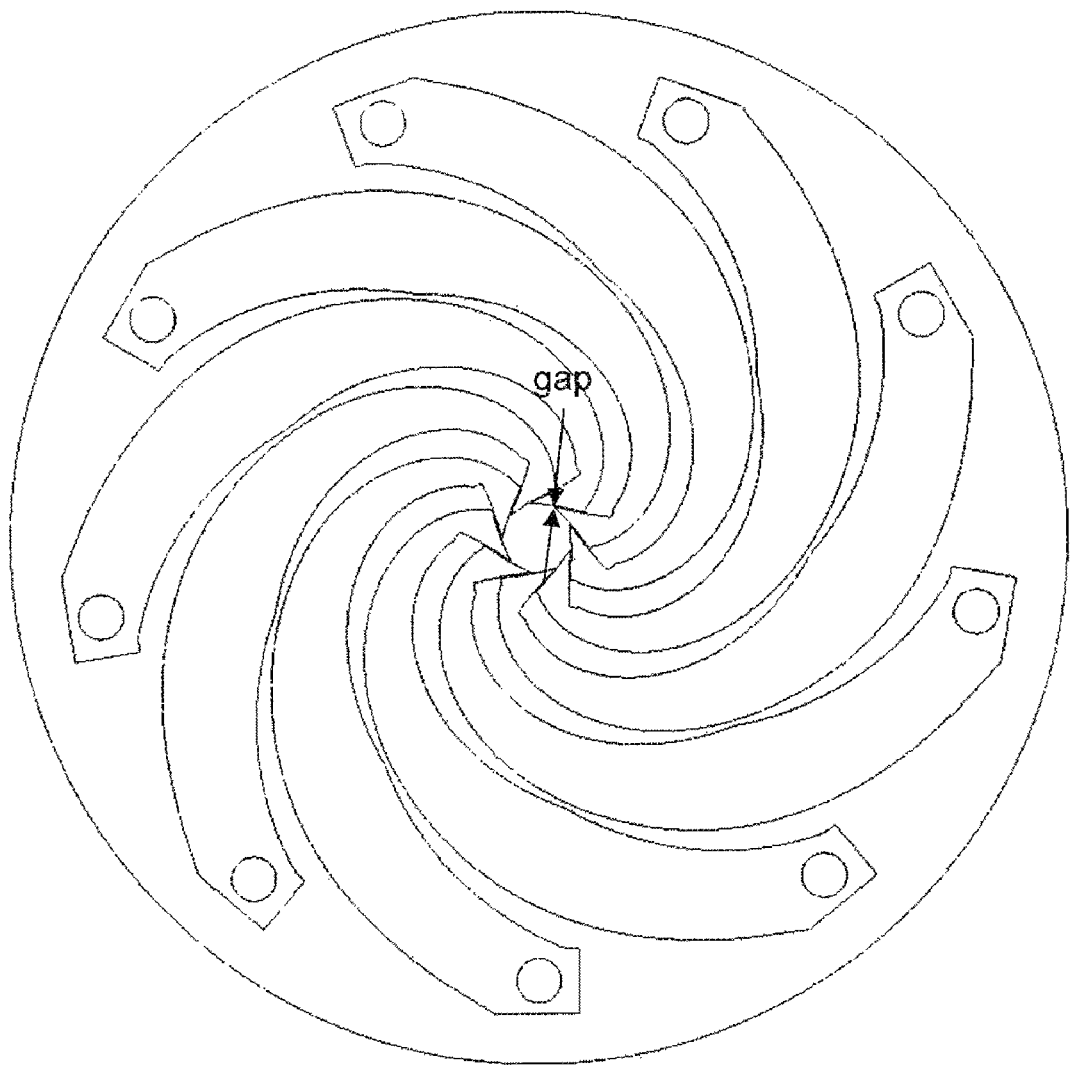
Figure 13 - Prior Art Type C in Partially-Open Position

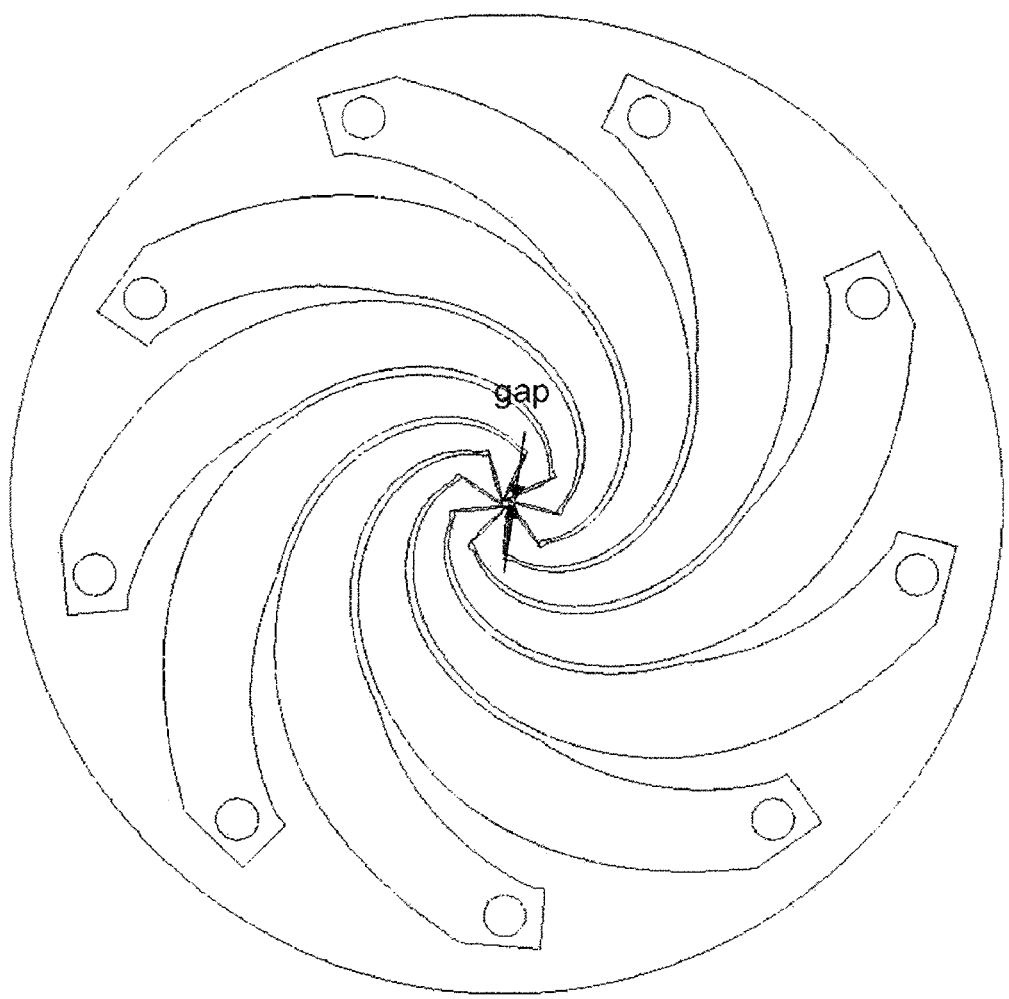
Figure 14 - Prior Art Type C Fully-Closed Position
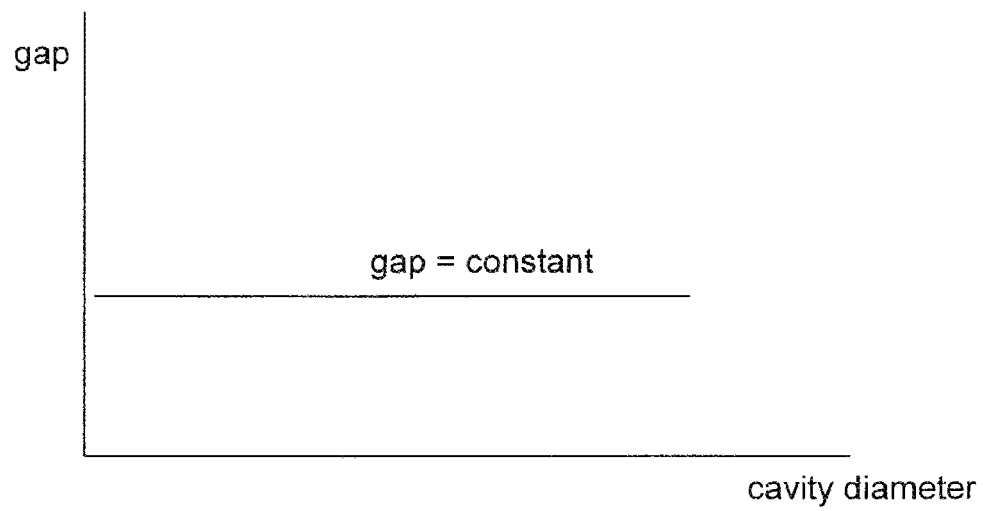
Figure 15 - Prior Art Type C Relationship Between Diameter and Gap

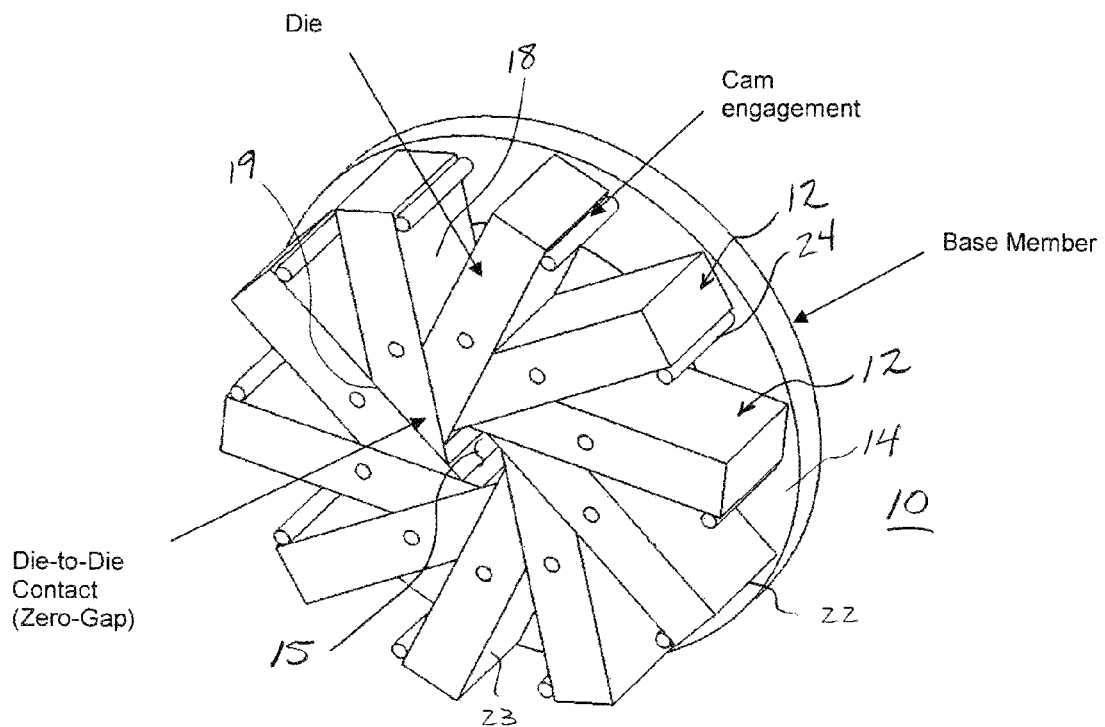
Figure 16 – Present Invention – Wedge-shaped dies located relative to each other with a cam engagement to a base member

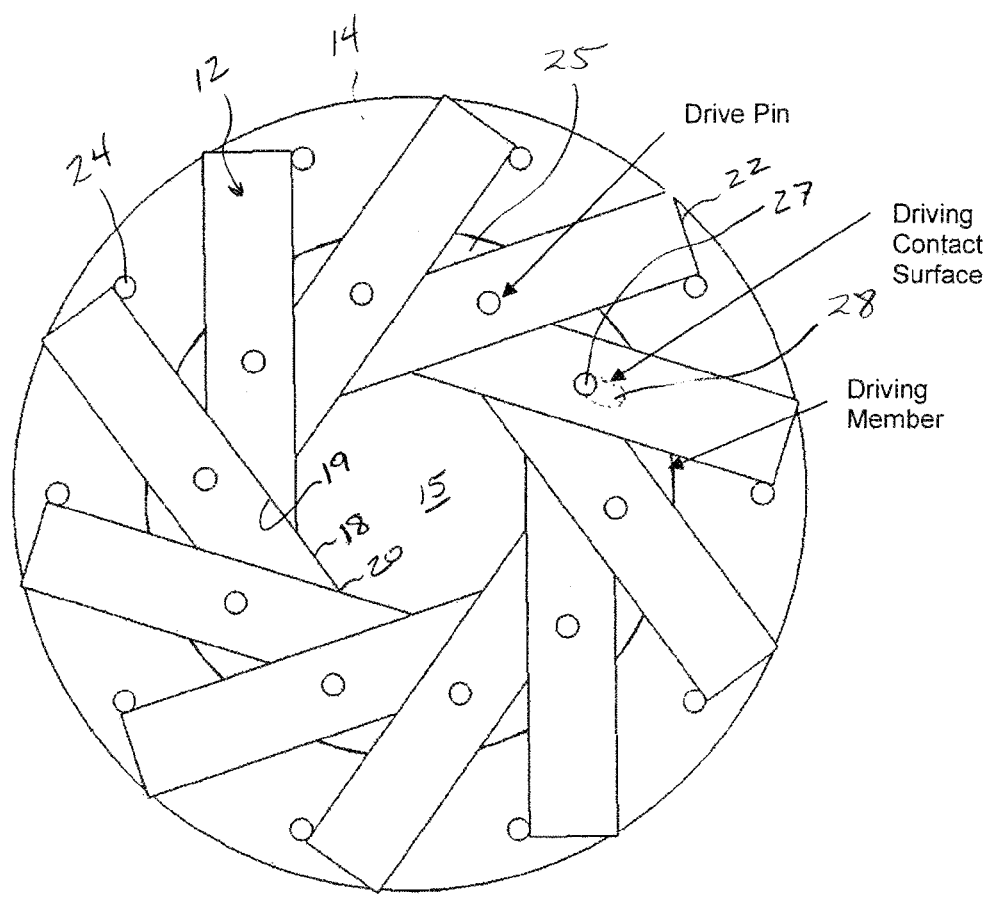
Figure 17 – Present Invention in Open Position Shown with Preferred Driving Method.

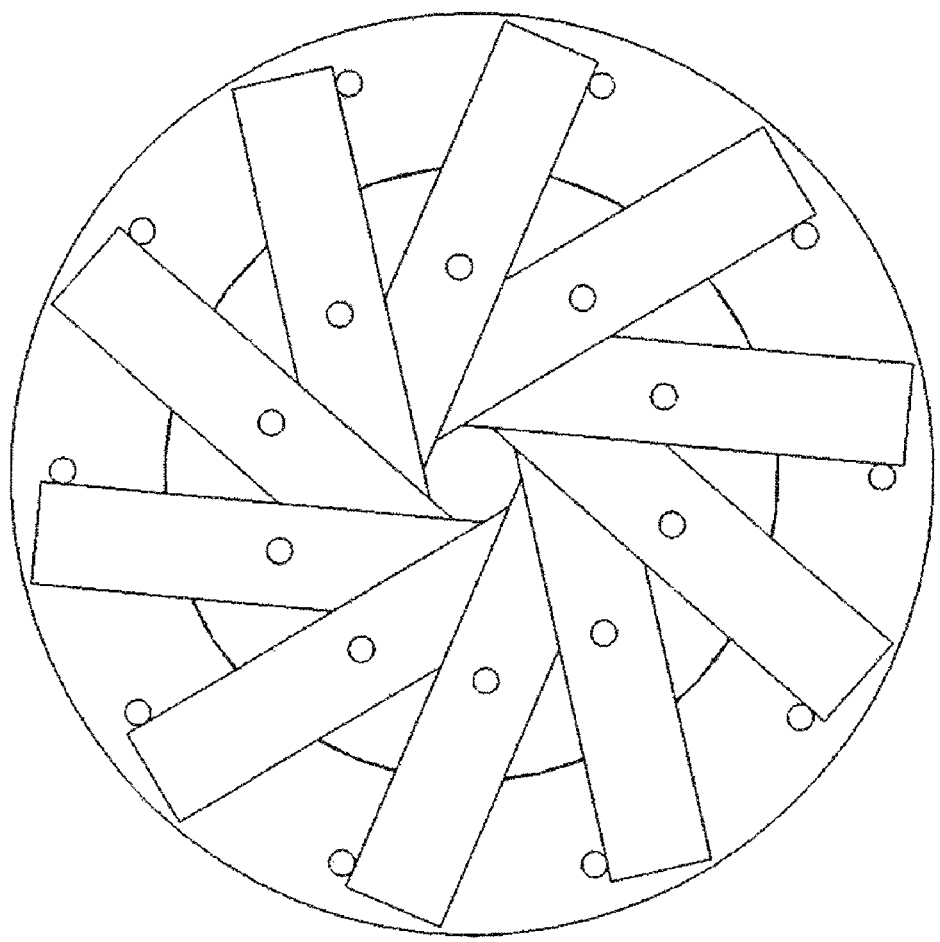
Figure 18 – Present Invention in Partially-Open Position

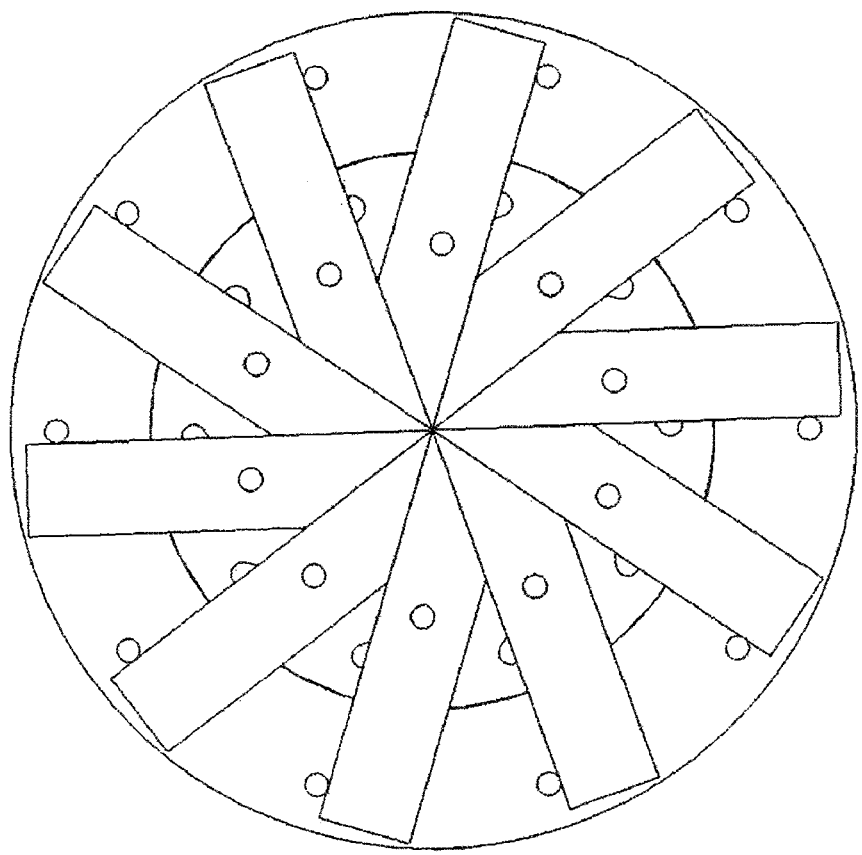
Figure 19 – Present Invention in Fully-Closed Position
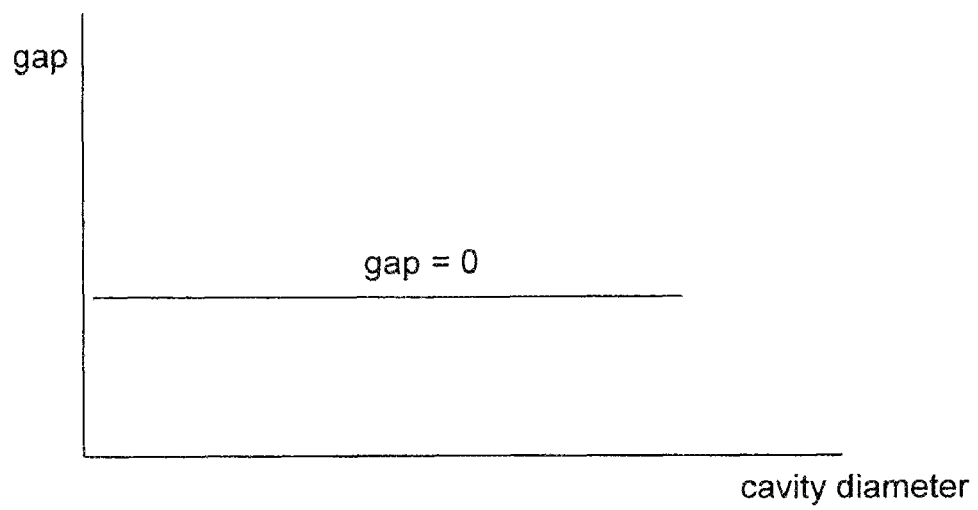
Figure 20 – Present Invention - Relationship Between Diameter and Gap

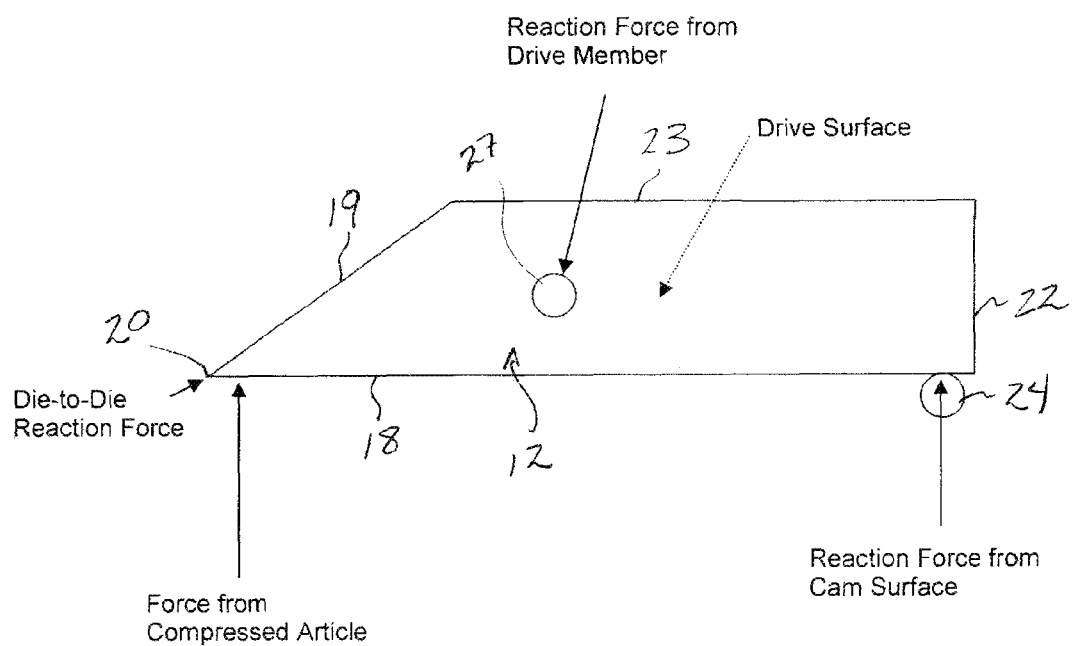
Figure 21 – Forces on Individual Die – Drive Surface is shaped so that the Die-to-Die Reaction Force is positive but nearly zero.

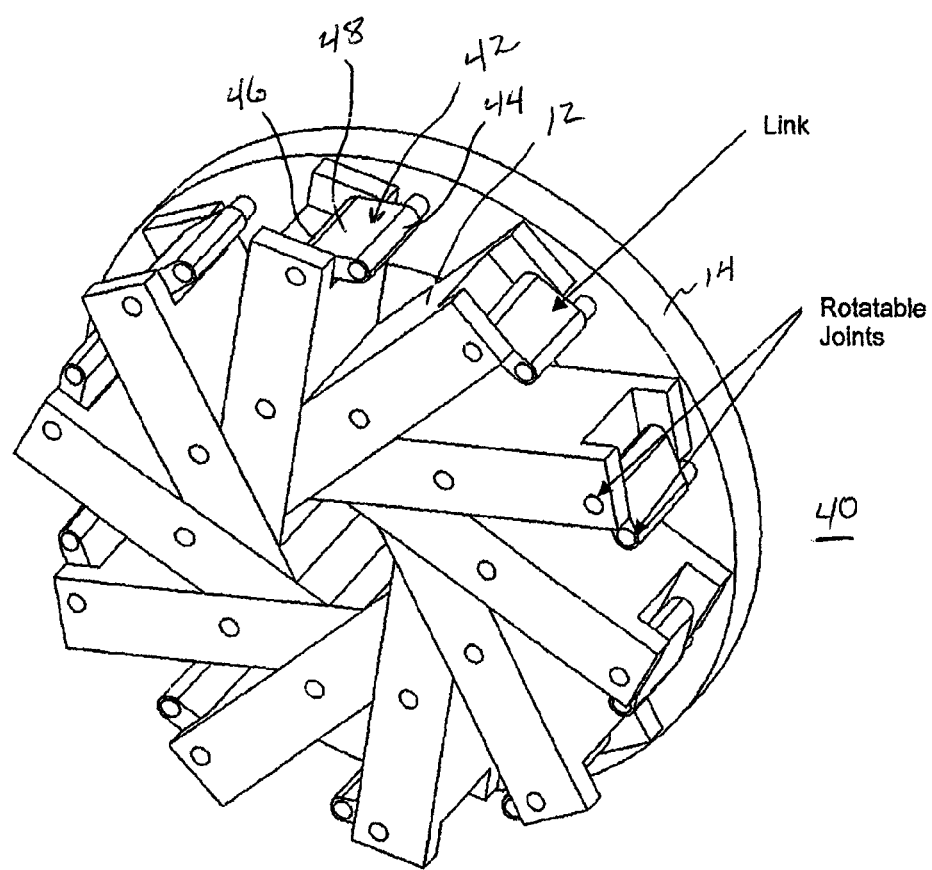
Figure 22 – Present Invention with Dies Connected via a Link to Common Base Member

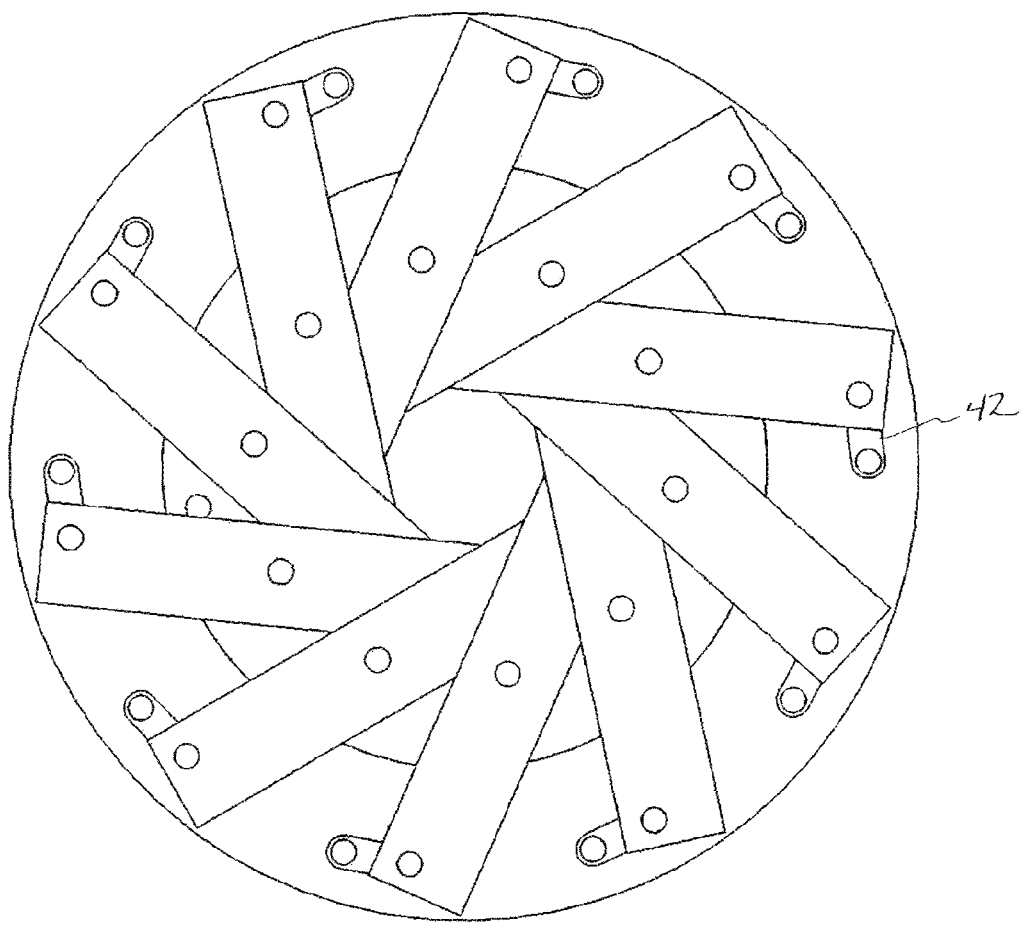
Figure 23 – Present Invention with Dies Connected via a Link to a Common Base Member

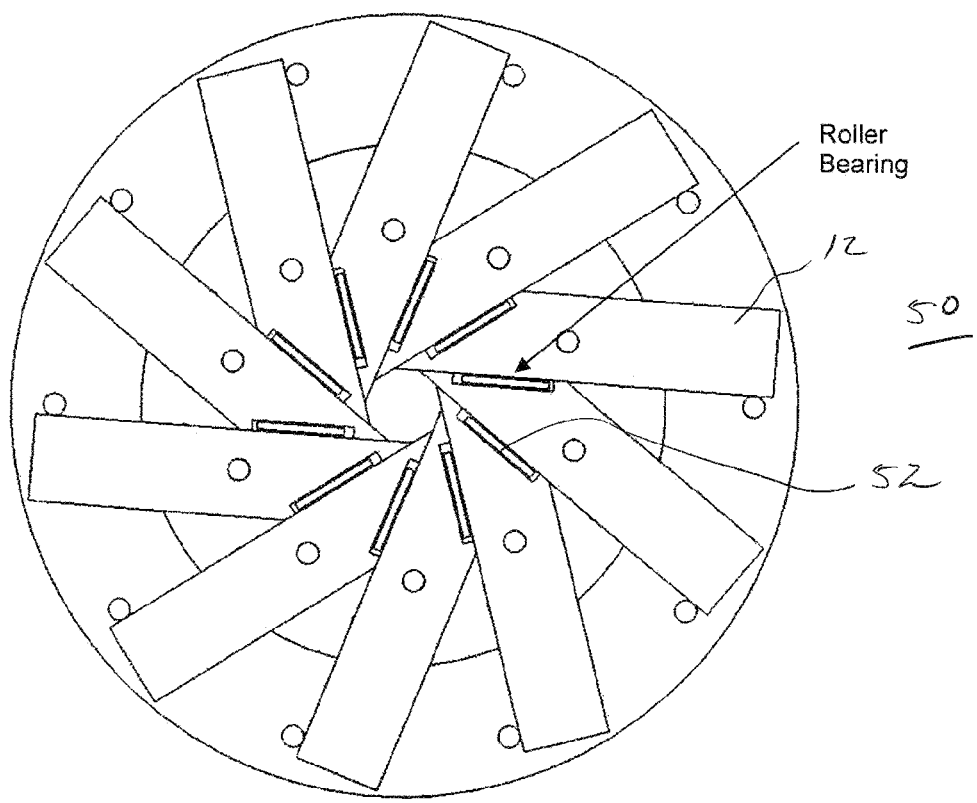
Figure 24 – Present Invention with Rolling Bearings between Die Surfaces to Reduce Friction.

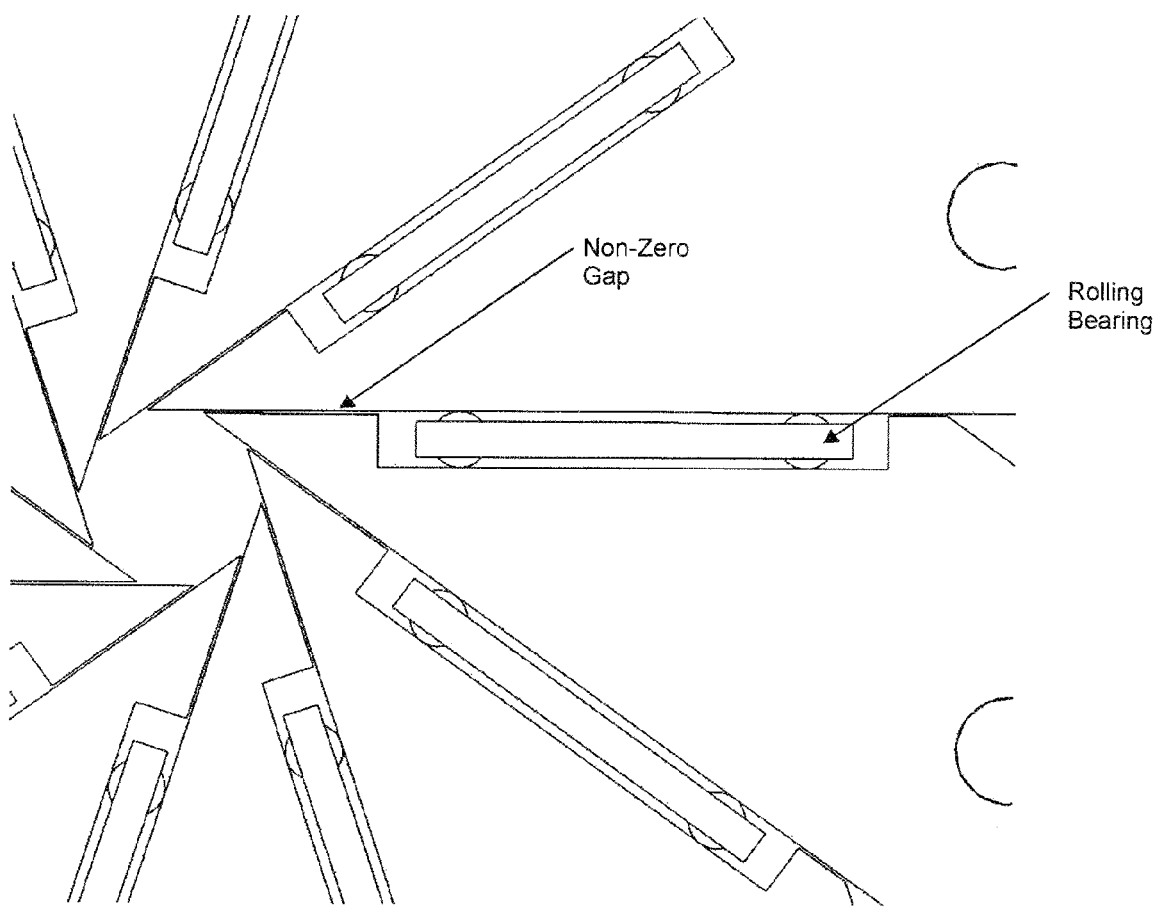
Figure 25 – Present Invention – Close-up view of Rolling bearings between die surfaces.
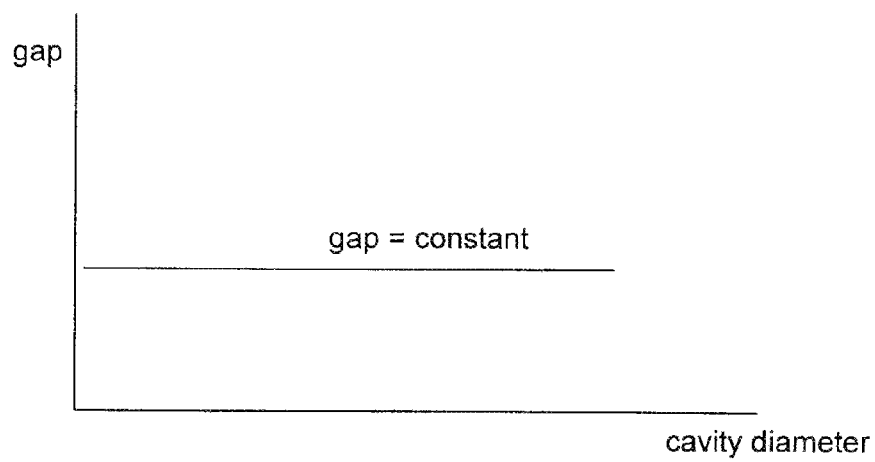
Figure 26 – Present Invention with Rolling Bearings - Relationship between Diameter and Gap

RADIAL COMPRESSION MECHANISM

CROSS-REFERENCE TO RELATED APPLICATION

This application claims the benefit of U.S. Provisional Application No. 60/888,662, filed 7 Feb. 2007.

FIELD OF THE INVENTION

This invention generally relates to radial compression mechanisms and more specifically to mechanisms for radially compressing devices such as stents, catheters, balloons, and the like.

BACKGROUND OF THE INVENTION

In the manufacture and testing of medical devices, mechanisms are used to radially compress cylindrical devices such as stents, balloons, and catheters. For example, installation of a stent into a catheter balloon is typically done by compressing the stent radially inward onto the balloon with enough pressure to permanently deform the stent to a smaller diameter and to slightly embed the metal stent into the plastic balloon. In another example, a polymer catheter balloon is compressed radially after pleating to wrap it tightly around the catheter shaft. In another example, a self-expanding stent is radially compressed to insert it into a sheath or delivery system. In an example of medical device testing, a stent is radially compressed while the required force is measured, in order to measure the stent's functional relationship between diameter and radial force.

A first type of prior art device includes a radial compression mechanism wherein several similar wedge-shaped dies with planar surfaces are arranged to form an approximately cylindrical central cavity, the wedges being hinged and driven in unison to change the diameter of the cavity. A mechanism of this type is illustrated in FIGS. 1 through 5. Examples of this mechanism are the Crimpfox tool sold by Phoenix Contact GmbH 7 Co. KG (CRIMPFOX UD 6-6, Part Number 1206366), and the "segmental compression mechanism" marketed by Machine Solutions Incorporated, and described in U.S. Pat. No. 6,968,607. In this type of mechanism, the working surfaces of the dies have a wedge shape with two planar surfaces meeting at the tip. The dies do not slide against each other but are rotated around a pivot point. A shortcoming of this type of mechanism is that there exists a gap between adjacent wedges, the size of which varies with the diameter of the cavity in an undesirable way. Typically, the mechanism is specifically designed to provide a desired range of cavity diameters. At the lowest and highest diameters, the dies are tightly wedged against each other (zero gap). As the diameter is increased from the lowest, the gap increases until it reaches a maximum, then decreases until it becomes zero again at the highest diameter, as illustrated graphically in FIG. 5. The diameter range and gap (as a function of diameter) depend on the specific design of the mechanism, particularly the location of the hinge or pivot point of the dies and the diameter of the circle formed by all of the die hinge points in the mechanism. A larger diameter of the hinge point circle results in a smaller maximum gap for a given diameter range. The strict design tradeoffs for this type of mechanism results in a mechanism that must be large to provide a small maximum gap for a given diameter range, or a mechanism that must have a large gap to provide the same diameter range in a small size. Large gaps between the wedges are a disadvantage because they allow space for parts of the compressed device to go into. For example, the metal struts of a stent can move into the gap and be damaged.

A second type of prior art device includes a radial compression mechanism wherein several similar wedge-shaped dies with planar surfaces are arranged to form an approximately cylindrical central cavity, the wedges being attached to linear guides and driven in unison to change the diameter of the central cavity. A mechanism of this type is illustrated in FIGS. 6 through 10. Examples of this mechanism include the mechanism taught by Kokish in U.S. Pat. No. 6,651,478, or the mechanism marketed by Interface Associates Inc. (Model W8FH). In this type of mechanism, the working surfaces of the dies have a wedge shape with two planar surfaces meeting at the tip. The linear motion of the wedges in this mechanism provides a wedge-to-wedge gap that is constant, independent of the cavity diameter, and may be designed to be any desired size (see FIG. 10). A shortcoming of this mechanism is that it typically does not provide a sufficiently accurate positional relationship of the wedge-shaped working ends of the dies. Accurate positional relationship of the dies is important so that the central cavity remains approximately round and provides even compression around the circumference of the compressed device, and so that the largest die-to-die gaps aren't much larger than the average. Because each die is carried on its own linear guide, and all of the guides are attached to a plate or base, many parts and attachments may influence the accuracy (roundness) of the central cavity. Medical device manufacturing and testing often requires an accurately round cavity at diameters as small as 0.5 mm. which is typically not achieved by this type of mechanism.

A third type of prior art includes a radial compression mechanism comprising several similarly-shaped dies arranged to form an approximately cylindrical central cavity, the dies being hinged (or pivoted) and driven in unison to change the diameter of the cavity. The working die surfaces are not planar, but have a specifically-designed shape that makes the gap between adjacent dies an arbitrary function of diameter that may be chosen by the designer. Typically, the gap is chosen to be approximately constant, independent of diameter, and as small as manufacturing tolerances will allow (see FIG. 15). Usually, the hinge point of each die is located approximately on the opposite side of the mechanism from the working tip of the die resulting in concave working surfaces. Examples of this mechanism include the mechanism marketed by Blockwise Engineering (Model RJ). A shortcoming of this device is that geometry of each of the dies in the preferred embodiment is difficult to manufacture accurately in non-metallic materials. Non-metallic dies are often required to limit the scoring or abrasion on the compressed article.

It would be highly advantageous, therefore, to remedy the foregoing and other deficiencies inherent in the prior art.

Accordingly, it is an object of the present invention to provide a new and improved radial compression mechanism for compressing devices such as stents, catheters, balloons, and the like in the medical industry.

Another object of the invention is to provide a new and improved radial compression mechanism utilizing radially movable dies that produce zero or nearly zero die-to-die gaps.

Another object of the invention is to provide a new and improved radial compression mechanism utilizing radially movable dies that produce a large usable size range.

An advantage of the present radial compression mechanism over prior art is that there is virtually no gap between dies since each of the dies contacts the neighboring dies.

Another advantage of the present radial compression mechanism over the first type of prior art is that there is no tradeoff between die-to-die gaping and the usable range of the central cavity diameter. Therefore, the mechanism can be designed with a relatively large diameter range for a given overall machine envelope.

An advantage of the present radial compression mechanism over the third type of prior art is that the geometry of the dies is much more simple to produce using conventional machining methods and can therefore be made from metallic and non-metallic materials.

SUMMARY OF THE INVENTION

Briefly, to achieve the desired objects and advantages of the present invention in accordance with a preferred embodiment thereof provided is radial compression mechanism including a base member and a plurality of elongated compression dies. Each die includes a planar base surface and a planar contact surface extending from a point to form an angle therebetween at one end of the die. The dies are arranged in a generally circular orientation on the base member with the contact surface of each die in sliding contact with the base surface of an adjacent die. A portion of each base surface of each die cooperates with portions of base surfaces of adjacent dies to define a generally cylindrical central cavity. The dies are further mounted for relative movement between an open position and a closed position. A driving mechanism is coupled to each die and designed to move the dies in unison between the open position and the closed position.

The dies are cammingly coupled to the base member and also cammingly coupled to a driving member. Rotation of the driving member about the central axis of the mechanism causes each die to move generally, but not precisely, arcuately about the point of camming engagement with the base member. The angles of cam contact are designed to provide a net inward force on each die, keeping it in contact with its neighbors.

The desired objects and advantages of the present invention are further achieved in accordance with a more specific embodiment of the present invention wherein the radial compression mechanism includes a base member and a plurality of elongated compression dies. Each individual die of the plurality of compression dies includes a planar base surface and a planar contact surface extending from a point to form an angle therebetween at one end of the individual die. Each die of the plurality of elongated compression dies is oriented with the one end directed generally inwardly and an opposite end directed generally outwardly. The dies are arranged in a generally circular orientation on the base member with the planar contact surface of each die being in sliding contact with the planar base surface of an adjacent die and a portion of each planar base surface of each die cooperating with portions of planar base surfaces of adjacent dies to define a generally cylindrical central cavity. The compression dies are further mounted for relative movement between a central cavity open position and a central cavity closed position. A driving mechanism is coupled to each die of the plurality of dies and designed to move the plurality of dies in unison between the central cavity open position and the central cavity closed position. The driving mechanism includes an arcuate camming surface, a cam follower pin associated with each individual die of the plurality of compression dies, and a driving member. The arcuate camming surface is formed on either one of the individual die and the driving member and the cam follower pin is attached to the other of the individual die and the driving member. The dies are cammingly coupled to the base member and also cammingly coupled to a driving member. Rotation of the driving member about the central axis of the mechanism causes each die to move generally, but not precisely, arcuately about the point of camming engagement with the base member. The angles of cam contact are designed to provide a net inward force on each die, keeping it in contact with its neighbors.

BRIEF DESCRIPTION OF THE DRAWINGS

The foregoing and further and more specific objects and advantages of the instant invention will become readily apparent to those skilled in the art from the following detailed description of a preferred embodiment thereof taken in conjunction with the drawings, in which:

FIGS. 1-4 illustrate a first type of prior art radial compression mechanism;

FIG. 5 illustrates graphically the relationship between the diameter of the central opening and die-to-die gaps for the embodiment of FIG. 1;

FIGS. 6-9 illustrate a second type of prior art radial compression mechanism with linear movement of the die;

FIG. 10 illustrates graphically the relationship between the diameter of the central opening and die-to-die gaps for the embodiment of FIG. 6;

FIGS. 11-14 illustrate another type of prior art radial compression mechanism;

FIG. 15 illustrates graphically the relationship between the diameter of the central opening and die-to-die gaps for the embodiment of FIGS. 11-14;

FIG. 16 is a receiving side view in perspective of a radial compression mechanism in accordance with the present invention;

FIG. 17 is a front plan view of the radial compression mechanism of FIG. 16 in a dilated position, some cam surfaces are illustrated in broken lines;

FIG. 18 is a front plan view of the radial compression mechanism of FIG. 16 in a partially contracted position;

FIG. 19 is a front plan view of the radial compression mechanism of FIG. 16 in the contracted position;

FIG. 20 illustrates graphically the relationship between the diameter of the central opening and die-to-die gaps for the embodiment of FIG. 16;

FIG. 21 is a side view of an individual die of the radial compression mechanism according to the present invention;

FIG. 22 is a receiving side view in perspective of another embodiment of a radial compression mechanism in accordance with the present invention;

FIG. 23 is a front plan view of the embodiment illustrated in FIG. 22;

FIG. 24 is a front plan view of a modification to the radial compression mechanism of FIG. 16;

FIG. 25 is an enlarged view of the rolling bearing of FIG. 24;

FIG. 26 illustrates graphically the relationship between the diameter of the central opening and die-to-die gaps for the embodiment of FIG. 24;

DETAILED DESCRIPTION OF A PREFERRED EMBODIMENT

Figure 27:
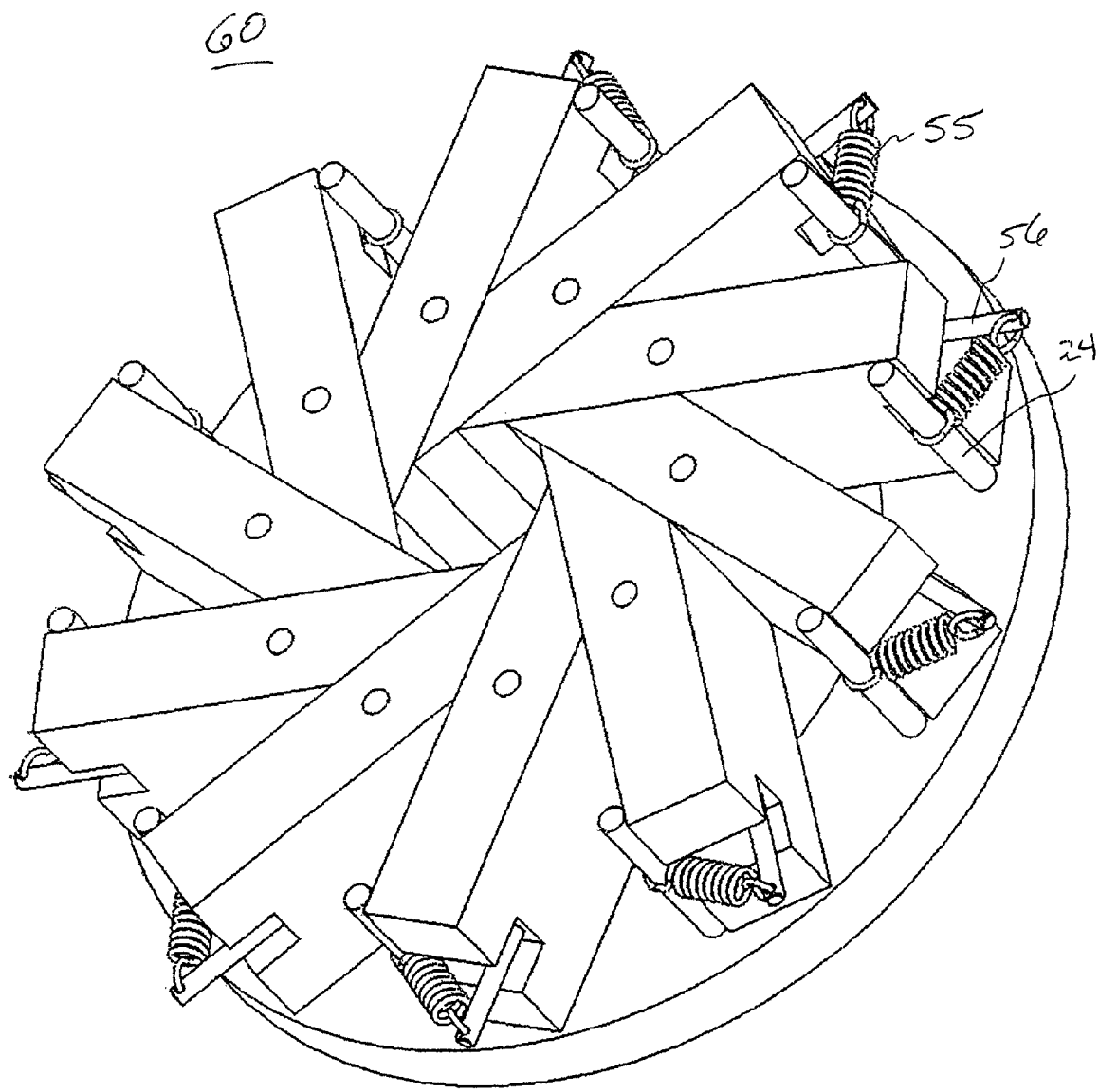
FIG. 27 is a receiving side view in perspective of another modification to the radial compression mechanism of FIG. 16, in accordance with the present invention.

Turning now to the drawings, FIGS. 1-4 illustrate an embodiment of the first type of prior art radial compression mechanism that is described in detail above in the Background of the Invention. FIGS. 6-9 illustrate an embodiment of the second type of prior art radial compression mechanism with linear movement of the die, also described in detail above in the Background of the Invention. FIGS. 11-14 illustrate an embodiment of the third type of prior art radial compression mechanism described in detail above in the Background of the Invention. Each of these types of devices operates in a known manner and will not be further discussed herein.

Turning now to FIGS. 16 through 21, attention is directed to FIG. 16 which illustrates a radial compression mechanism in accordance with the present invention, generally designated 10. Mechanism 10 includes a plurality of compression dies 12 carried by a base member 14. Each die 12 is of a generally identical wedge shape, and is arranged with adjacent dies to form a generally cylindrical central cavity 15. As is understood, cylindrical central cavity 15 is designed to receive devices such as stents, catheters, balloons, and the like for radial compression. For example, installation of a stent into a catheter balloon is typically done by compressing the stent radially inward onto the balloon with enough pressure to permanently deform the stent to a smaller diameter and to slightly embed the metal stent into the plastic balloon. In another example, a polymer catheter balloon is compressed radially after pleating to wrap it tightly around the catheter shaft. In another example, a self-expanding stent is radially compressed to insert it into a sheath or delivery system. In each of these examples cylindrical central cavity 15, and mechanism 10, must be constructed to dilate sufficiently to receive the device to be compressed and must be constructed to contract smoothly and sufficiently to perform the desired compression.

Referring specifically to FIG. 21, a single die 12 of mechanism 10 is illustrated. As shown, each die 12 includes divergent planar surfaces 18 and 19, diverging from a point 20, which form the wedge shape of each die 12. Surface 18 extends away from point 20 and terminates at an end 22. Surface 19 extends away from point 20 and terminates at a sidewall 23 substantially extending to end 22 parallel to surface 18. Planar surface 18 of each die 12 contacts planar surface 19 of an adjacent die 12, locating each die 12 relative to its neighbors. Dies 12 are carried by base member 14 and are in a camming engagement therewith. A camming pin 24 extends from base adjacent each die 12 and cammingly engages a planar surface of the die, for example, as shown in FIG. 21, planar surface 18 proximate end 22. As will be described presently, dies 12 are driven in unison to change the diameter of cavity 15 between a dilated position (FIG. 17) and a contracted position (FIG. 19). The number of dies may vary over a practical range of 3 to 20 and there are many possible means to drive the dies in unison.

In the embodiment illustrated, ten dies 12 cooperate to define cylindrical central cavity 15, thus the angle defined between planar surfaces 18 and 19 is approximately 36 degrees. It will be understood that this angle will vary as the number of dies in mechanism 10 varies. Also, for purposes of this description, planar surface 18, which extends in a plane from point 20 to end 22, is referred to as the "base surface" and planar surface 19, which is oriented at an angle to base surface 18, is referred to as the "contact surface". To define central cavity 15, a portion of each planar base surface 18 of each die 12 cooperates with portions of planar base surfaces 18 of adjacent dies 12 to define generally cylindrical central cavity 15. The length of the portion of each planar base surface 18 of each die 12 determines the diameter of central cavity 15 in the open position.

As illustrated in FIG. 17, mechanism 10 also includes a drive mechanism for moving dies 12 between the dilated or open position (illustrated in FIG. 17) and the contracted or closed position (illustrated in FIG. 19). In the preferred embodiment, dies 12 are driven in unison by the use of a wheel or disk 25. Disk 25 is rotated about an axis through the center of central cavity 15 (the center of mechanism 10). Drive pins 27 are attached to and extend perpendicularly from each die 12 generally intermediate point 20 and end 22. Drive pins 27 are received in engaging arcuate slots 28 (illustrated in broken lines), also referred to as camming surfaces, on disk 25 and operate as cam follower pins. Disk 25 is rotationally driven to open or close central cavity 15 by the action of moving or camming drive pins 27 to follow arcuate slots 28.

The driving mechanism, including drive pins 27 and arcuate slots 28, is designed to move each individual die 12 generally, but not precisely, arcuately about the point of camming engagement with base member 14. For example in the embodiment illustrated in FIG. 17 rotation of disk 25 in the clockwise direction cams points 20 of dies 12 inwardly and closes or contracts central cavity 15 and rotation of disk 25 in the counterclockwise direction cams points 20 of dies 12 outwardly and opens or dilates central cavity 15. The guidance of each die by contact with neighboring dies, as opposed to the prior art linear movement, provides a much more accurate positional relationship of the working ends of dies 12. Further, because the sliding die-to-die contact does not cause the dies to collide with each other, as opposed to the prior-art hinged-wedge mechanism, movement between the open and closed positions can be extended to allow for a much larger diameter central cavity 15. In an alternative embodiment (not shown), drive pins 27 can be attached to rotating disk 25, and engage slots or camming surfaces on dies 12. Power to drive disk 25 may be, for example, human muscles, an electric motor, a fluid-powered motor and the like.

The shape of slots or camming surfaces 28 determines the relationship between the force applied to the article to be compressed within cavity 15, and the die-to-die force. In the preferred embodiment, slots or surfaces 28 are designed such that a force applied to the compressed article in cavity 15 results in a positive but nearly zero die-to-die force (i.e. the force between planar surface 19 of one die and planar surface 18 of the adjacent die). Keeping the die-to-die force positive is necessary to keep dies 12 in contact with each other. At the same time, low die-to-die force is desired to minimize wear and friction between dies.

As can be seen in FIGS. 16, 17, and 18, the plurality of compression dies 12 are arranged in a generally circular orientation with contact surface 19 of each die 12 being in sliding contact with base surface 18 of an adjacent die 12 with a portion of each base surface 18 adjacent tip 20 of each die 12 of the plurality of dies cooperating to define central cavity 15. Because contact surface 19 of each die 12 is in contact with base surface 18 of the adjacent die 12 there is virtually no gap between dies 12. Also, because base surface 18 and contact surface 19 are planar surfaces, there is no tradeoff between die-to-die gaping and the usable range of the central cavity diameter. Further, by forming camming surfaces 28 smooth and arcuate, mechanism 10 is constructed to contract smoothly and efficiently between the open position and the closed position to perform the desired compression.

Turning now to FIGS. 22 and 23, another embodiment of a radial compression mechanism generally designated 40 is illustrated. In this embodiment, mechanism 40 is substantially the same as mechanism 10 and similar components are designated with similar numbers. The cam engagement of each of dies 12 to common base member 14 is replaced with a linkage 42. Linkage 42 includes two rotatable joints 44 and 46 and a link 48. Rotatable joint 44 pivotally connects link 48 to die 12 and rotatable joint 46 pivotally connects link 48 to common base member 14. Thus, linkage 42 permits a generally identical movement of dies 12 as that of mechanism 10 and the camming engagement of cam 24.

Turning now to FIGS. 24 and 25, another embodiment of a radial compression mechanism generally designated 50 is illustrated. In this embodiment, components that are similar to components in mechanism 10 are designated with similar numbers and the structures are similar except for the change explained below. Mechanism 50 consists of outfitting each die-to-die contact surfaces 18 and 19 with a low friction bearing 52. In the preferred embodiment, bearing 52 is set into contact surface 19 but could be alternatively set into base surface 18 if desired. Bearing 52 could be a plain bearing, or incorporate rollers or ball bearings or bearing surfaces such as Teflon and the like. An advantage of this embodiment is that the frictional force between the dies could be significantly lower as compared to other embodiments. A disadvantage of this embodiment is that the mechanism may be more complex and there may be a non-zero gap between the die-surfaces that form the central cavity. The non-zero gap can be substantially eliminated if bearing 52 is a bearing surface rather than a mechanical bearing. The non-zero gap, if present, is typically designed to be as small as manufacturing tolerances allow.

Figure 28:
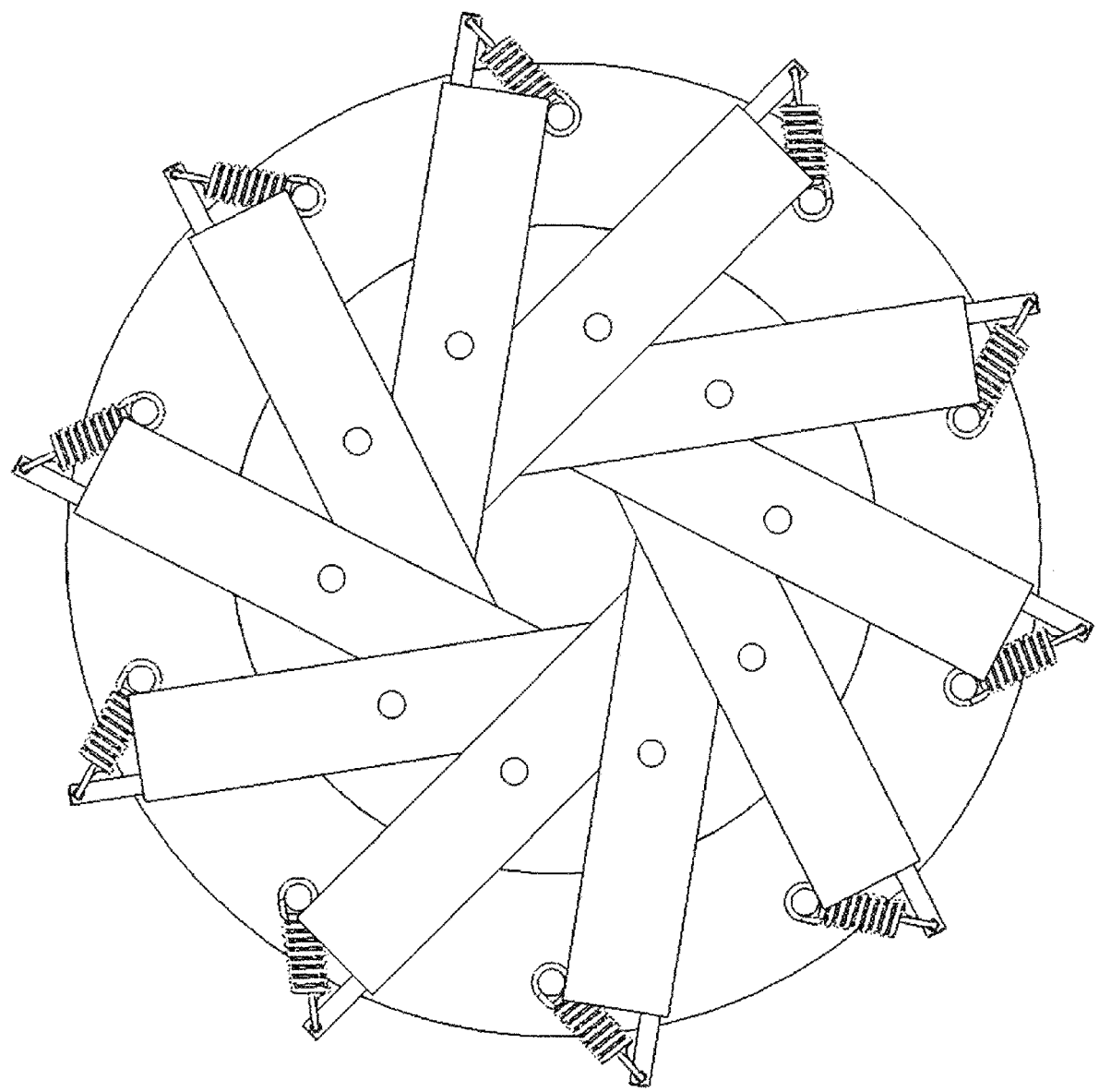
FIG. 28 is a front plan view of the embodiment illustrated in FIG. 27.

Turning now to FIGS. 27 and 28, another embodiment of a radial compression mechanism generally designated 60 is illustrated. In this embodiment, components that are similar to components in mechanism 10 are designated with similar numbers and the structures are similar except for the change explained below. With reference to mechanism 60, the contact surfaces 19 of dies 12 are biased into engagement with base surfaces 18 of adjacent or neighboring dies by a tension spring 55 attached to a post 56 extending from end 22 and cam 24. An advantage of mechanism 60 over other embodiments is that springs 25 keep the positive die-to-die force relatively constant and can be adjusted to any desired amount of tension.

Thus, a new and improved radial compression mechanism for compressing devices such as stents, catheters, balloons, and the like in the medical industry has been disclosed. One major advantage of this mechanism over the prior art is that there is virtually no gap between dies since each of the dies contacts the neighboring dies. Another advantage of this mechanism is that there is no tradeoff between die-to-die gaping and the usable range of the central cavity diameter. Therefore, the mechanism can be designed with a relatively large diameter range for a given overall machine envelope. Another advantage of this mechanism is that the geometry of the dies is much simpler to produce using conventional machining methods and can therefore be made from metallic and non-metallic materials.

Various changes and modifications to the embodiments herein chosen for purposes of illustration will readily occur to those skilled in the art. To the extent that such modifications and variations do not depart from the spirit of the invention, they are intended to be included within the scope thereof, which is assessed only by a fair interpretation of the following claims.

Having fully described the invention in such clear and concise terms as to enable those skilled in the art to understand and practice the same, the invention claimed is:

The invention claimed is:

1. Radial compression mechanism comprising:
   a base member;
   a plurality of elongated compression dies, each individual die of the plurality of compression dies including a planar base surface and a planar contact surface extending from a point to form an angle therebetween at one end of the individual die, each die of the plurality of compression dies being cammingly coupled to the base member and defining a camming point;
   the plurality of compression dies being arranged in a generally circular orientation on the base member with the planar contact surface of each die being in sliding contact with the planar base surface of an adjacent die and a portion of each planar base surface of each die cooperating with portions of planar base surfaces of adjacent dies to define a generally cylindrical central cavity, the plurality of compression dies being further mounted for relative movement between a central cavity open position and a central cavity closed position; and
   a driving mechanism formed to rotate about a central axis of the mechanism, the driving mechanism cammingly coupled to each die of the plurality of compression dies and designed to move the plurality of compression dies in unison between the central cavity open position and the central cavity closed position, rotation of the driving mechanism moves each individual die of the plurality of compression dies generally arcuately about the camming point of the individual die, angles of cam contact being designed to provide a net inward force on each individual die to keep each individual die in contact with neighboring dies.

2. Radial compression mechanism as claimed in claim 1 wherein the number of compression dies in the plurality of compression dies is in a range of three to twenty dies.

3. Radial compression mechanism as claimed in claim 1 wherein the driving mechanism includes an arcuate camming surface and a cam follower pin associated with each individual die of the plurality of compression dies, the arcuate camming surface being formed directly on one of the individual die and a driving member and the cam follower pin being directly attached to the other of the individual die and the driving member.

4. Radial compression mechanism as claimed in claim 3 wherein the arcuate camming surface is designed to produce a positive force between the planar contact surface of each die and the planar base surface of the adjacent die as force is applied to a compressed article in the central cavity.

5. Radial compression mechanism as claimed in claim 1 wherein the length of the portion of each planar base surface of each die determines the diameter of the central cavity in the open position.

6. Radial compression mechanism as claimed in claim 1 further including a plurality of camming pins attached to the base member, one camming pin of the plurality of camming pins associated with each individual die of the plurality of compression dies, the one camming pin associated with each individual die being positioned in a camming orientation adjacent an end of the individual die opposite the one end.

7. Radial compression mechanism as claimed in claim 1 further including linkage associated with an end of each individual die opposite the one end, the linkage coupling the associated individual die to the base member and guiding movement of the individual die between the open and closed positions.

8. Radial compression mechanism as claimed in claim 7 wherein the linkage includes two rotatable joints and a link therebetween, one of the two rotatable joints pivotally connecting the link to the base member and the other rotatable joint of the two rotatable joints connecting the link to the die.

9. Radial compression mechanism as claimed in claim 1 further including a bearing positioned between the planar contact surface of each die in sliding contact with the planar base surface of the adjacent die.

10. Radial compression mechanism comprising:
- a base member;
- a plurality of elongated compression dies, each individual die of the plurality of compression dies including a planar base surface and a planar contact surface extending from a point to form an angle therebetween at one end of the individual die, each die of the plurality of elongated compression dies being oriented with the one end directed generally inwardly and an opposite end directed generally outwardly;
- the plurality of compression dies being arranged in a generally circular orientation on the base member, each die of the plurality of compression dies being cammingly engaged with the base member, the planar contact surface of each die being in sliding contact with the planar base surface of an adjacent die and a portion of each planar base surface of each die cooperating with portions of planar base surfaces of adjacent dies to define a generally cylindrical central cavity, the plurality of compression dies being further mounted for relative movement between a central cavity open position and a central cavity closed position; and
- a driving mechanism coupled to each die of the plurality of compression dies and designed to move the plurality of compression dies in unison between the central cavity open position and the central cavity closed position, the driving mechanism including an arcuate camming surface, a cam follower pin associated with each individual die of the plurality of compression dies, and a driving member, the arcuate camming surface being formed on one of the individual die and the driving member and the cam follower pin being attached to the other of the individual die and the driving member, the driving mechanism being designed to move each individual die generally arcuately about a camming point of the individual die.

11. Radial compression mechanism as claimed in claim 10 wherein the number of compression dies in the plurality of compression dies is in a range of three to twenty dies.

12. Radial compression mechanism as claimed in claim 10 wherein the arcuate camming surface is designed to produce a positive force between the planar contact surface of each die and the planar base surface of the adjacent die as force is applied to a compressed article in the central cavity.

13. Radial compression mechanism as claimed in claim 10 wherein the length of the portion of each planar base surface of each die determines the diameter of the central cavity in the open position.

14. Radial compression mechanism as claimed in claim 10 further including a plurality of camming pins attached to the base member, one camming pin of the plurality of camming pins associated with each individual die of the plurality of compression dies, the one camming pin associated with each individual die being positioned in a camming orientation adjacent an end of the individual die opposite the one end.

15. Radial compression mechanism as claimed in claim 10 further including linkage associated with an end of each individual die opposite the one end, the linkage coupling the associated individual die to the base member and guiding movement of the individual die between the open and closed positions.

16. Radial compression mechanism as claimed in claim 15 wherein the linkage includes two rotatable joints and a link therebetween, one of the two rotatable joints pivotally connecting the link to the base member and the other rotatable joint of the two rotatable joints connecting the link to the die.

17. Radial compression mechanism as claimed in claim 10 further including a bearing positioned between the planar contact surface of each die in sliding contact with the planar base surface of the adjacent die.

* * * * *